(12) United States Patent
Kohler et al.

(10) Patent No.: US 7,569,674 B2
(45) Date of Patent: Aug. 4, 2009

(54) AUTOPHILIC ANTIBODIES

(75) Inventors: Heinz Kohler, Lexington, KY (US); Sybille Muller, Lexington, KY (US)

(73) Assignee: InNexus Biotechnology International Limited, Scottsdale, AZ (US)

( * ) Notice: Subject to any disclaimer, the term of this patent is extended or adjusted under 35 U.S.C. 154(b) by 348 days.

(21) Appl. No.: 11/119,404

(22) Filed: Apr. 29, 2005

(65) Prior Publication Data

US 2005/0287154 A1 Dec. 29, 2005

Related U.S. Application Data

(63) Continuation-in-part of application No. 10/652,864, filed on Aug. 29, 2003, and a continuation-in-part of application No. 09/865,281, filed on May 29, 2001, now abandoned, which is a continuation-in-part of application No. 09/070,907, filed on May 4, 1998, now Pat. No. 6,238,667.

(60) Provisional application No. 60/407,421, filed on Aug. 30, 2002.

(51) Int. Cl.
*C12P 21/08* (2006.01)
*C07K 16/00* (2006.01)
*A61K 39/395* (2006.01)
*C12P 21/04* (2006.01)
*C07H 21/04* (2006.01)

(52) U.S. Cl. .............. 530/387.3; 424/133.1; 424/141.1; 424/146.1; 424/155.1; 435/69.6; 503/388.1; 503/388.26; 503/388.8; 503/388.85

(58) Field of Classification Search ................ None
See application file for complete search history.

(56) References Cited

U.S. PATENT DOCUMENTS

| | | |
|---|---|---|
| 5,191,066 A | 3/1993 | Bieniarz et al. |
| 5,219,996 A | 6/1993 | Bodmer et al. |
| 5,276,170 A | 1/1994 | Kirk et al. |
| 5,314,995 A | 5/1994 | Fell, Jr. et al. |
| 5,563,046 A | 10/1996 | Mascarenhas et al. |
| 5,596,081 A | 1/1997 | Haley et al. |
| 5,645,835 A | 7/1997 | Fell, Jr. et al. |
| 5,668,255 A | 9/1997 | Murphy |
| 5,677,171 A | 10/1997 | Hudziak et al. |
| 5,698,679 A | 12/1997 | Nemazee |
| 5,763,733 A | 6/1998 | Whitlow et al. |
| 5,800,991 A | 9/1998 | Haley et al. |
| 5,807,746 A | 9/1998 | Lin et al. |
| 5,811,265 A | 9/1998 | Quertermous et al. |
| 5,908,626 A | 6/1999 | Chang et al. |
| 5,969,109 A | 10/1999 | Bona et al. |
| 6,008,319 A | 12/1999 | Epstein et al. |
| 6,043,339 A | 3/2000 | Lin et al. |
| 6,117,656 A | 9/2000 | Seed |
| 6,121,424 A | 9/2000 | Whitlow et al. |
| 6,132,992 A | 10/2000 | Ledbetter et al. |
| 6,207,804 B1 | 3/2001 | Huston et al. |
| 6,218,160 B1 | 4/2001 | Duan |
| 6,224,870 B1 | 5/2001 | Segal |
| 6,228,603 B1 | 5/2001 | Reed et al. |
| 6,235,667 B1 | 5/2001 | Paloschi et al. |
| 6,238,667 B1 * | 5/2001 | Kohler ................ 424/179.1 |
| 6,248,558 B1 | 6/2001 | Lin et al. |
| 6,287,537 B1 | 9/2001 | Kaminski et al. |
| 6,312,694 B1 | 11/2001 | Thorpe et al. |
| 6,316,003 B1 | 11/2001 | Frankel et al. |
| 6,406,693 B1 | 6/2002 | Thorpe et al. |
| 6,426,413 B1 | 7/2002 | Wannamaker et al. |
| 6,432,680 B1 | 8/2002 | Lin et al. |
| 6,482,586 B1 | 11/2002 | Arab et al. |
| 6,566,338 B1 | 5/2003 | Weber et al. |
| 6,596,693 B1 | 7/2003 | Keana et al. |
| 6,620,782 B1 | 9/2003 | Cai et al. |
| 6,716,410 B1 | 4/2004 | Witztum et al. |
| 6,762,045 B2 | 7/2004 | Krebs et al. |
| 6,780,605 B1 | 8/2004 | Frostegard et al. |
| 6,821,274 B2 | 11/2004 | McHale et al. |
| 7,041,459 B2 | 5/2006 | Singh et al. |
| 2002/0143142 A1 | 10/2002 | Lin et al. |
| 2003/0103984 A1 | 6/2003 | Kohler |
| 2003/0143226 A1 | 7/2003 | Kobayashi et al. |
| 2003/0148265 A1 | 8/2003 | Brooks et al. |

(Continued)

FOREIGN PATENT DOCUMENTS

WO WO-9617625 6/1996

(Continued)

OTHER PUBLICATIONS

Lederman et al. Molecular Immunology 28:1171-1181, 1991.*

(Continued)

*Primary Examiner*—David J. Blanchard
(74) *Attorney, Agent, or Firm*—Gifford, Krass, Sprinkle, Anderson & Citkowski, P.C.

(57) ABSTRACT

Antibodies having noncovalent, autophilic properties are disclosed. The autophilic antibodies are derived from antibodies conjugated with an autophilic peptide. Such autophilic antibodies can promote apoptosis of target cells and enhance therapeutic efficacies in the treatment of patients with diseases or disorders responsive to antibody therapy. Compositions containing the antibodies, and methods of making and using the antibodies are also disclosed.

6 Claims, 14 Drawing Sheets

U.S. PATENT DOCUMENTS

| | | |
|---|---|---|
| 2004/0185039 A1 | 9/2004 | Kohler et al. |
| 2005/0033033 A1 | 2/2005 | Kohler et al. |
| 2006/0233790 A1 | 10/2006 | Futaki et al. |

FOREIGN PATENT DOCUMENTS

| | | |
|---|---|---|
| WO | WO-9620219 | 7/1996 |
| WO | WO-9914244 | 3/1999 |
| WO | WO-0160866 | 8/2001 |
| WO | WO02097041 | 12/2002 |
| WO | WO-03080115 | 10/2003 |
| WO | WO-2006119291 | 11/2006 |

OTHER PUBLICATIONS

Li et al. Proc. Natl. Acad. Sci. USA 77:3211-3214, 1980.*

Nakamura et al. Cancer Research, 54(6):1511-1516, 1994.*

Bendig M. M. Methods: A Companion to Methods in Enzymology, 8:83-93, 1995.*

Ghetie, M. et al., "Homodimerization of tumor-reactive monoclonal antibodies markedly increases their ability to induce growth arrest or apoptosis of tumor cells," *PNAS USA*, (1997) 94; pp. 7509-7514.

Kang, C-Y, et al. "Inhibition of self-binding antibodies (autobodies) by a VH-derived peptide," *Science*, (1988) 240:1034-1036.

Kang, C-Y, et al, "Immunoglobulin with complementary paratope and idiotype," *J. Exp. Med.* (1986) 163: 787.

Kaveri, S., et al., "Antibodies of different specificities are self-binding: implication for antibody diversity," *Mol. Immunol.*, (1991) 2: 733-78.

Kaveri, S., et al., "Self-binding antibodies (autobodies) form specific complexes in solution," *J. Immunol.* (1990) 145: 2533-2538.

Kohler, H., et al., "Superantibody activities: new players in innate and adaptive immune responses," *Immun. Today*, (1998) 19:221-227.

Kohler, H., "Superantibodies: synergy of innate and acquired immunity," *Appl. Biochem. Biotechnol.*, (2000) 83: 1-9.

Lin, Y., et al, "Inhibition of nuclear translocation of transcription factor NF-kB by a synthetic peptide containing a cell membrane-permeable motif and nuclear localization sequence," J. *Biol Chem*, (1995) 270: 14255-14258.

Muller, S., et al., "TransMabs: cell-penetrating antibodies, the next generation," *Expert Opin. Biol. Ther.*, (2005) 5: 237-241.

Rojas, M., et al., "Genetic engineering of proteins with cell membrane permeability," *Nat. Biotechnol.*, (1998) 16: 370-375.

Zhao, Y., et al., "Chemical engineering of cell penetrating antibodies," *J. Immun. Methods*, (2001) 254: 137-145.

Zhao, Y., et al., "Enhancing tumor targeting and apoptosis using noncovalent antibody homodimers," *J. Immunotherapy*, (2002) 25(5): 1-9.

Zhao, Y., et al., "Enhanced Anti-B-cell Tumor Effects with Anti-CD20 Superantibody," *J. Immunotherapy*, (2002) 25: 57-62.

Binder, M., F. Otto, R. Mertelsmann, H. Veelken, and M. Trepel. "The epitope recognized by rituximab." Blood 2006, vol. 108, No. 6, pp. 1975-1978.

Braendstrup, P., O.W. Bjerrum, O.J. Nielsen, B.A. Jensen, N.T. Clausen, P.B. Hansen, I. Andersen, K. Schmidt, T.M. Andersen, N.A. Peterslund, H.S. Birgens, T. Plesner, B.B. Pedersen, and H.C. Hasselbalch. "Rituximab Chimeric Anti-CD20 Monoclonal Antibody Treatment for Adult Refractory Idiopathic Thrombocytopenic Purpura." American Journal of Hematology 2005, vol. 78, pp. 275-280.

Burton, C., R. Kaczmarski, R. Jan-Mohamed. "Interstitial Pneumonitis Related to Rituximab Therapy." The New England Journal of Medicine 2003, vol. 348, No. 26, pp. 2690-2691.

Edwards, J.C.W., L. Szczepanski, J. Szechinski, A. Filipowicz-Sosnowska, P. Emery, D.R. Close, R.M. Stevens, and T. Shaw. "Efficacy of B-Cell-Targeted Therapy with Rituximab in Patients with Rheumatoid Arthritis." The New England Journal of Medicine 2004, vol. 350, No. 25, pp. 2572-2581.

Pandey, R.N., L.E. Davis, B. Anderson, and P.F. Hollenberg. "Photochemical linking of primary aromatic amines to carrier proteins to elicit antibody response against the amine haptens." Journal of Immunological Methods 1986, vol. 94, pp. 237-246.

Lambris, J.D., V.S. Ganu, S. Hirani, and H.J. Muller-Eberhard. "Mapping the C3d receptor (CR2)-binding site and a neoantigenic site in the C3d domain of the third component of complement." Proceedings of the National Academy of Sciences USA 1985, vol. 82, pp. 4235-4239.

Frankel, A.E. "Antibody-Toxin Hybrids: A Clinical Review of Their Use." Journal of Biological Response Modifiers 1985, vol. 4, pp. 437-446.

Chaddock, J.A., L.M. Roberts, B. Jungnickel, and J. Michael Lord. "A hydrophobic region of ricin a chain which may have a role in membrane translocation can function as an efficient noncleaved signal peptide." Biochemical and Biophysical Research Communications 1995, vol. 217, No. 1, pp. 68-73.

Morris, K.N. and I.G. Wool. "Analysis of the contribution of an amphiphilic α-helix to the structure and to the function of ricin A chain." Proceedings of the National Academy of Sciences USA 1994, vol. 91, pp. 7530-7533.

Kohler, H., G. Pavlinkova, K. Rajagopalan, H-T. Wang, S. Chatterjee, and B. Haley. "Specific photoaffinity-labeling locus on antibodies: use for chelation, protein conjugation and gene delivery." Journal of Cellular Biochemistry Supplement, Abstract T029, No. 18D, 1994, pp. 189.

Pavlinkova, G., K. Rajagopalan, S. Muller, A. Chavan, G. Sievert, D. Lou, C. O'Toole, B. Haley, and H. Kohler. "Site-specific photobiotinylation of immunoglobulins, fragments and light chain dimers." Journal of Immunological Methods 1997, vol. 201, pp. 77-88.

Miles, E.W. and R.S. Phillips. "Photoinactivation and Photoaffinity Labeling of Tryptophan Synthase $\alpha_2\beta_2$ Complex by the Product Analogue 6-Azido-L-tryptophan." Biochemistry 1985, vol. 24, pp. 4694-4703.

Rousselot, P., E. Mappus, T. Blachere, M. Rolland de Ravel, C. Grenot, C. Tonnelle, and C.Y. Cuilleron. "Specific Photoaffinity Labeling of Tyr-49 on the Light Chain in the Steroid-Combining Site of a Mouse Monoclonal Anti-Estradiol Antibody Using Two Epimeric 6α- and 6β-(5-Azido-2-nitrobenzoyl)amidoestradiol Photoreagents." Biochemistry 1997, vol. 36, pp. 7860-7868.

Fleet, G.W.J., J.R. Knowles, and R.R. Porter. "The Antibody Binding Site: Labelling of a Specific Antibody Against the Photo-Precursor of an Aryl Nitrene." Biochemistry Journal 1972, vol. 128, pp. 499-508.

Lou, D. and H. Kohler. "Enhanced molecular mimicry of CEA using photoaffinity crosslinked C3d peptide." Nature Biotechnology 1998, vol. 16, pp. 458-462.

Demoliou, C.D. and R.M. Epand. "Synthesis and Characterization of a Heterobifunctional Photoaffinity Reagent for Modification of Tryptophan Residues and its Application to the Preparation of a Photoreactive Glucagon Derivative." Biochemistry 1980, vol. 19, pp. 4539-4546.

Foxwell, B.M.J., W.C.J. Ross, and P.E. Thorpe. "Antibody-Ricin Conjugates: A Method of Linkage which Blocks the Galactose Binding Site of Ricin." Behring Institute Mitteilungen 1984, No. 74, pp. 101-107.

Tao, M-H. and R. Levy. "Idiotype/granulocyte-macrophage colony-stimulating factor fusion protein as a vaccine for B-cell Lymphoma." Nature 1993, vol. 362, pp. 755-758.

Johnston, A., G.R. Auda, M.A. Kerr, M.W. Steward, and K. Whaley. "Dissociation of primary antigen-antibody bonds is essential for complement mediated solubilization of immune precipitates." Molecular Immunology 1992, vol. 29, No. 5, pp. 659-665.

Thorpe, P.E. and W.C.J. Ross. "The Preparation and Cytotoxic Properties of Antibody-Toxin Conjugates." Immunological Review 1982, vol. 62 pp. 119-158.

Zhao, Y., T.L. Brown, H. Kohler, and S. Muller. "MTS-conjugated-antiactive caspase 3 antibodies inhibit actinomycin D-induced apoptosis." Apoptosis 2003, vol. 8, pp. 631-637.

Hallbrink, M., A. Floren, A. Elmquist, M. Pooga, T. Bartfai, U. Langel. "Cargo delivery kinetics of cell-penetrating peptides." Biochimica et Biophysica Acta 2001, vol. 1515, pp. 101-109.

Soomets, U., M. Lindgren, X. Gallet, M. Hallbrink, A. Elmquist, L. Balaspiri, M. Zorko, M. Pooga, R. Brasseur, U. Langel. "Deletion analogues of transportan." Biochimica et Biophysica Acta 2000, vol. 1467, pp. 165-176.

Fischer, P.M., N.Z. Zhelev, S. Wang, J.E. Melville, R. Fahraeus, D.P. Lane. "Structure-activity relationship of truncated and substituted analogues of the intracellular delivery vector Penetratin." Journal of Peptide Research 2000, vol. 55, pp. 163-172.

Lindberg, M., J. Jarvet, U. Langel, and A. Graslund. "Secondary Structure and Position of the Cell-Penetrating Peptide Transportan in SDS Micelles As Determined by NMR." Biochemistry 2001, vol. 40, pp. 3141-3149.

Li, Y. R. V. Rosal, P.W. Brandt-Rauf, and R.L. Fine. "Correlation between hydrophobic properties and efficiency of carrier-mediated membrane transduction and apoptosis of a p53 C-terminal peptide." Biochemical and Biophysical Research Communications 2002, vol. 298, pp. 439-449.

Zanetti, M. "Antigenized antibodies." Nature 1992, vol. 355, pp. 476-477.

Zaghouani, H., S.A. Anderson, K.E. Sperber, C. Daian, R.C. Kennedy, L. Mayer, and C.A. Bona. "Induction of antibodies to the human immunodeficiency virus type 1 by immunization of baboons with immunoglobulin molecules carrying the principal neutralizing determinant of the envelope protein." Proceedings of the National Academy of Science USA 1995, vol. 92, pp. 631-635.

Kang, C., H. Cheng, S. Rudikoff, and H. Kohler. "Idiotypic self binding of a dominant germline idiotype (T15)." Journal of Experimental Medicine 1987, vol. 165, pp. 1332-1343.

Yan, X., S.V. Evans, M.J. Kaminki, S.D. Gillies, R.A. Reisfeld, A.N. Houghton, and P.B. Chapman, "Characterization of an Ig $V_H$ Idiotype That Results in Specific Homophilic Binding and Increased Avidity for Antigen." The Journal of Immunology 1996, vol. 157, pp. 1582-1588.

Dempsey, P.W., M.E.D. Allison, S. Akkaraju, C.C. Goodnow, D.T. Fearon. "C3d of Complement as a Molecular Adjuvant: Bridging Innate and Acquired Immunity." Science 1996, vol. 271, pp. 348-350.

Antoni, G., R. Presentini, F. Perin, A. Tagliabue, P. Ghiara, S. Censini, G. Volpini, L. Villa, and D. Boraschi. "A short synthetic peptide fragment of human interleukin 1 with immunostimulatory but not inflammatory activity." The Journal of Immunology 1986, vol. 137, pp. 3201-3204.

Bhattacharya-Chatterjee, M., S. Mukerjee, W. Biddle, K.A. Foon, and H. Kohler. "Murine monoclonal anti-idiotype antibody as a potential network antigen for human carcinoembryonic antigen." The Journal of Immunology 1990, vol. 145, pp. 2758-2765.

Foon, K., M. Chakraborty, W.J. John, A. Sherratt, H. Kohler, and M. Bhattacharya-Chatterjee. "Immune Response to the Carcinoembryonic Antigen in Patients Treated with an Anti-Idiotype Antibody Vaccine." Journal of Clinical Investigation 1995, vol. 96, pp. 334-342.

Kaminski, M.S., K. Kitamura, and D.G. Maloney, and R. Levy. "Idiotype Vaccination Against Murin B cell Lymphoma. Inhibition of Tumor Immunity by Free Idiotype Protein." The Journal of Immunology 1987, vol. 138, pp. 1289-1296.

Abaza, M. and M.Z. Atassi. "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin." Journal of Protein Chemistry 1992, vol. 11, pp. 433-444.

Rojas, M. S. Yao, and Y.Z. Lin, "Controlling Epidermal Growth Factor (EGF)-stimulated Ras Activation in Intact Cells by a Cell-permeable Peptide Mimicking Phosphorylated EGF Receptor." The Journal of Biological Chemistry 1996, vol. 271, No. 44.

Gerstmayer, B., U. Altenschmidt, M. Hoffman, and W. Wels. "Costimulation of T Cell Proliferation by a Chimeric B7-2 Antibody Fusion Protein Specifically Targeted to Cells Expressig the erbB2 Proto-Oncogene." Journal of Immunology 1997, vol. 158, pp. 4584-4590.

Allison, A.C. "The Mode of Action of Immunological Adjuvants." Developments in Biological Standardization 1998, vol. 92, pp. 3-11.

Awwad, M., P.G. Strome, S.C. Gilman, H.R. Axelrod. "Modification of monoclonal antibody carbohydrate by oxidation, conjugation, or deoxymannojirimycin does not interfere with antibody effector functions." Cancer Immunology Immunotherapy 1994, vol. 38, pp. 23-30.

Binder, C.J., S. Horkko, A. Dewan, M. Chang, E.P. Kieu, C.S. Goodyear, P.X. Shaw, W. Palinski, J.L. Witztum, and G.J. Silverman. "Pneumococcal vaccination decreases atherosclerotic lesion formation: molecular mimicry between *Streptococcus pneumoniae* and oxidized LDL." Nature Medicine 2003, vol. 9, pp. 736-743.

Stein, S., A. Weiss, K. Adermann, P. Lazarovici, J. Hochman, H. Wellhoner, "A disulfide conjugate between anti-tetanus antibodies and HIV (37-72)Tat neutralizes tetanus toxin inside chromaffin cells," FEBS Letters, vol. 458, 1999, pp. 383-386.

Richardson, J.H. and W.A. Marasco. "Intracellular antibodies: development and therapeutic potential." TIBTECH 1995, vol. 13, pp. 306-310.

* cited by examiner

```
                         SEQUENCE LISTING

<160> NUMBER OF SEQ ID NOS: 7

<210> SEQ ID NO 1
<211> LENGTH: 25
<212> TYPE: PRT
<213> ORGANISM: mouse

<400> SEQUENCE: 1

Ala Ser Arg Asn Lys Ala Asn Asp Tyr Thr Thr Asp Tyr Ser Ala Ser
1               5                   10                  15

Val Lys Gly Arg Phe Ile Val Ser Arg
            20                  25

<210> SEQ ID NO 2
<211> LENGTH: 17
<212> TYPE: PRT
<213> ORGANISM: mouse

<400> SEQUENCE: 2

Lys Gly Glu Gly Ala Ala Val Leu Leu Pro Val Leu Leu Ala Ala Pro
1               5                   10                  15

Gly

<210> SEQ ID NO 3
<211> LENGTH: 28
<212> TYPE: PRT
<213> ORGANISM: Artificial sequence
<220> FEATURE:
<223> OTHER INFORMATION: T15 peptide - scrambled

<400> SEQUENCE: 3

Ser Tyr Ser Ala Ser Arg Phe Arg Lys Asn Gly Ser Ile Arg Ala Val
1               5                   10                  15

Glu Ala Thr Thr Asp Val Asn Ser Ala Tyr Ala Lys
            20                  25

<210> SEQ ID NO 4
<211> LENGTH: 24
<212> TYPE: PRT
<213> ORGANISM: Artificial sequence
<220> FEATURE:
<223> OTHER INFORMATION: T15 peptide - scrambled

<400> SEQUENCE: 4

Ser Lys Ala Val Ser Arg Phe Asn Ala Lys Gly Ile Arg Tyr Ser Glu
1               5                   10                  15

Thr Asn Val Asp Thr Tyr Ala Ser
            20

<210> SEQ ID NO 5
<211> LENGTH: 17
<212> TYPE: PRT
<213> ORGANISM: Artificial sequence
<220> FEATURE:
<223> OTHER INFORMATION: R24 peptide

<400> SEQUENCE: 5
```

-continued

```
Gly Ala Ala Val Ala Tyr Ile Ser Ser Gly Gly Ser Ser Ile Asn Tyr
1               5                   10                  15
Ala

<210> SEQ ID NO 6
<211> LENGTH: 18
<212> TYPE: PRT
<213> ORGANISM: Artificial sequence
<220> FEATURE:
<223> OTHER INFORMATION: R24 - charged peptide

<400> SEQUENCE: 6

Gly Lys Ala Val Ala Tyr Ile Ser Ser Gly Gly Ser Ser Ile Asn Tyr
1               5                   10                  15

Ala Glu

<210> SEQ ID NO 7
<211> LENGTH: 18
<212> TYPE: PRT
<213> ORGANISM: Artificial sequence
<220> FEATURE:
<223> OTHER INFORMATION: MTS optimized peptide

<400> SEQUENCE: 7

Trp Lys Gly Glu Ser Ala Ala Val Ile Leu Pro Val Leu Ile Ala Ser
1               5                   10                  15

Pro Gly
```

AUTOPHILIC ANTIBODIES

REFERENCE TO RELATED APPLICATIONS

This application is a continuation-in-part of U.S. patent application Ser. No. 10/652,864, filed 29 Aug. 2003, which claims the benefit of U.S. Provisional Patent Application No. 60/407,421 filed 30 Aug. 2002, and is a continuation-in-part of U.S. patent application Ser. No. 09/865,281, filed 29 May 2001, now abandoned which is a continuation-in-part of U.S. patent application Ser. No. 09/070,907, filed 4 May 1998, now U.S. Pat. No. 6,238,667.

TECHNICAL FIELD

The present invention relates to antibodies, compositions containing antibodies, and methods of using the antibodies and compositions in the treatment of a variety of diseases, including those diseases treatable with passive antibody therapy.

BACKGROUND

Antibodies have emerged as a major therapeutic tool for the treatment of chronic diseases such as cancer and autoimmune disorders. One of the principal advantages of these biological agents lies in their ability to target disease-causing cells or molecules, while sparing healthy tissue and normal products of the body. However, antibodies that exhibit desired specificities often fail in pre-clinical and clinical evaluations because of inefficient targeting and/or low therapeutic activity.

A rare class of antibodies, known as SuperAntibodies, exist in nature. These are antibodies that exhibit one or more properties not usually associated with antibodies (Kohler H., et al., 1998; Kohler H., 2000). The defined class of SuperAntibodies comprises catalytic, membrane-penetrating, and autophilic antibodies and includes many antibodies exhibiting superior targeting and therapeutic properties. One example of a naturally occurring SuperAntibody is the murine TEPC-15 antibody. TEPC-15 is an autophilic antibody which targets a normally cryptic determinant of phosphorylcholine on apoptotic cells and atherosclerotic lesions. TEPC-15 antibodies have high therapeutic efficacy due to their ability to form dimers or multimers (on cell or bacteria surfaces, after binding to antigen), which enhances apoptosis. TEPC-15 antibodies are able to form dimers and multimers due to an autophilic peptide sequence. (Kang, C-Y, et al., 1988)

It is known that a major mechanism by which therapeutic antibodies attack their target cells is through the induction of apoptosis. Apoptosis is triggered by crosslinking cellular receptors that are part of the apoptosis signal pathway. For example, crosslinking the B-cell antigen receptor by means of antibodies induces apoptosis in B-cell tumors (Ghetie M., et al., 1997). Crosslinking of cellular receptors also increases the binding avidity of an antibody to its target antigen, and thus is likely to increase all cell surface-dependent therapeutic mechanisms, such as complement-mediated killing and complement-dependent opsonization and phagocytosis, antibody-dependent cellular cytotoxicity (ADCC), as well as enhanced inhibition of cell growth or alterations in metabolic pathways within cells through increased binding to and blockade of cellular receptors when using antibodies targeted to cellular receptors.

To enhance the therapeutic efficacy of known antibodies, others have proposed the use of hybrid molecules for therapeutic purposes wherein the hybrid molecules comprise two distinct domains covalently linked. For instance, U.S. Pat. No. 6,482,586 (issued to Arab et al.) proposes covalent hybrid compositions for use in intracellular targeting. U.S. Pat. No. 6,406,693 (issued to Thorpe et al.) proposes antibodies and conjugates for killing tumor vascular endothelial cells by binding to aminophospholipid on the luminal surface.

These are but a few of the approaches that have been used to enhance therapeutic efficacy of monoclonal antibodies that, in their native or "humanized" state, are not effective in killing their targets or triggering a biological function affording therapeutic efficacy.

There is a need for a method of enhancing the therapeutic efficacy of antibodies which have desired specificities without the use of toxic agents.

SUMMARY OF INVENTION

The present invention is directed to autophilic antibodies, compositions containing autophilic antibodies, methods of making autophilic antibodies, methods of restoring autophilic activity to antibodies that have lost that activity, methods of assaying target antigens for autophilic antibodies, methods of enhancing apoptosis, complement fixation or cell-mediated killing using the autophilic antibodies, and methods of using the autophilic antibodies and compositions in the treatment of various diseases responsive to antibody therapy. The diseases include those treatable with passive antibodies, including atheroschlerosis, cancers, autoimmune disorders, Alzheimer's disease and other neuro-degenerative conditions, as well as artifacts of a functioning immune system such as graft or transplant rejection.

The present invention relates to antibodies having autophilic properties that mimic those of rare, naturally occurring, autophilic antibodies. Autophilic antibodies according to the present invention have the unusual property of spontaneously binding to one another after first binding to their target antigen (differential oligomerization).

The antibodies can comprise any antibody conjugated with an autophilic peptide sequence. In some embodiments, the antibodies are capable of binding an antigen, which, when bound, has a therapeutic effect on a disease state or disorder. In some specific embodiments, the antibodies comprise 5D10, S1C5, anti-caspase antibodies, anti-CD20 antibodies such as rituximab, IF5, and tositumomab, anti-GM2 antibodies, humanized S107, trastuzumab, humanized TEPC-15, and humanized R24.

The antibodies can be conjugated with any autophilic peptide which allows the antibodies to dimerize or oligomerize once bound to an antigen. The peptide can comprise any autophilic peptide sequence. In specific embodiments, the peptide comprises the T15 peptide sequence, the T15-scr2 peptide sequence, the R24 peptide sequence, the R24-charged peptide sequence, and optimized versions thereof.

Autophilic antibodies can also be conjugated with one or more other peptides to add additional functionality. In one embodiment, the autophilic antibodies can be conjugated to an autophilic peptide sequence and a transmembrane peptide sequence which allows the autophilic antibodies to penetrate inside cells and bind to intracellular targets. In specific embodiments, the transmembrane peptide sequence comprises MTS peptide or MTS-optimized peptide.

The invention also relates to compositions containing one or more autophilic antibodies of the invention and pharmaceutically acceptable carriers. The compositions can be administered to patients in need of treatment with the autophilic antibodies of the invention. The compositions can be optimized to prevent the autophilic antibodies from forming spontaneous dimers before administration.

The antibodies and compositions containing antibodies of the invention can be administered in doses similar to, or lower than, those practicable for non-autophilic antibodies.

The autophilic antibodies of the invention are preferably formed by one of several methods, including chemically crosslinking a peptide capable of self-binding to an antibody. In a specific embodiment, the peptide is cross-linked to an antibody through oxidation of an N-linked carbohydrate. Alternatively, the autophilic peptide can be linked to an antibody through the nucleotide binding site or to a tryptophane binding site, or through less specific methods, such as through antibody epsilon amino groups or sulfhydryl groups obtained through partial reduction of the antibody.

The invention also relates to a method of optimizing autophilic peptide sequences for use in forming autophilic antibodies comprising optimizing a template-peptide.

The invention also relates to a method of restoring autophilic properties to an antibody, such as a humanized antibody, which has lost its autophilic properties, in whole or in part, during the humanization process, by conjugating an autophilic peptide to the antibody as described above.

The invention also contemplates a method for assaying target antigens for autophilic antibodies, and a method of testing the efficacy of autophilic antibodies using animal models.

The invention also relates to methods of enhancing apoptosis, complement fixation, or cell-mediated killing using the autophilic antibodies of the invention comprising administering the antibodies of the invention.

The invention also relates to a method of treating a patient suffering from a disorder, disease, or condition responsive to passive antibody therapy comprising administering an autophilic antibody of the invention to the patient.

BRIEF DESCRIPTION OF DRAWINGS

In drawings which are intended to illustrate embodiments of the invention.

DETAILED DESCRIPTION OF THE INVENTION

Figure 1:
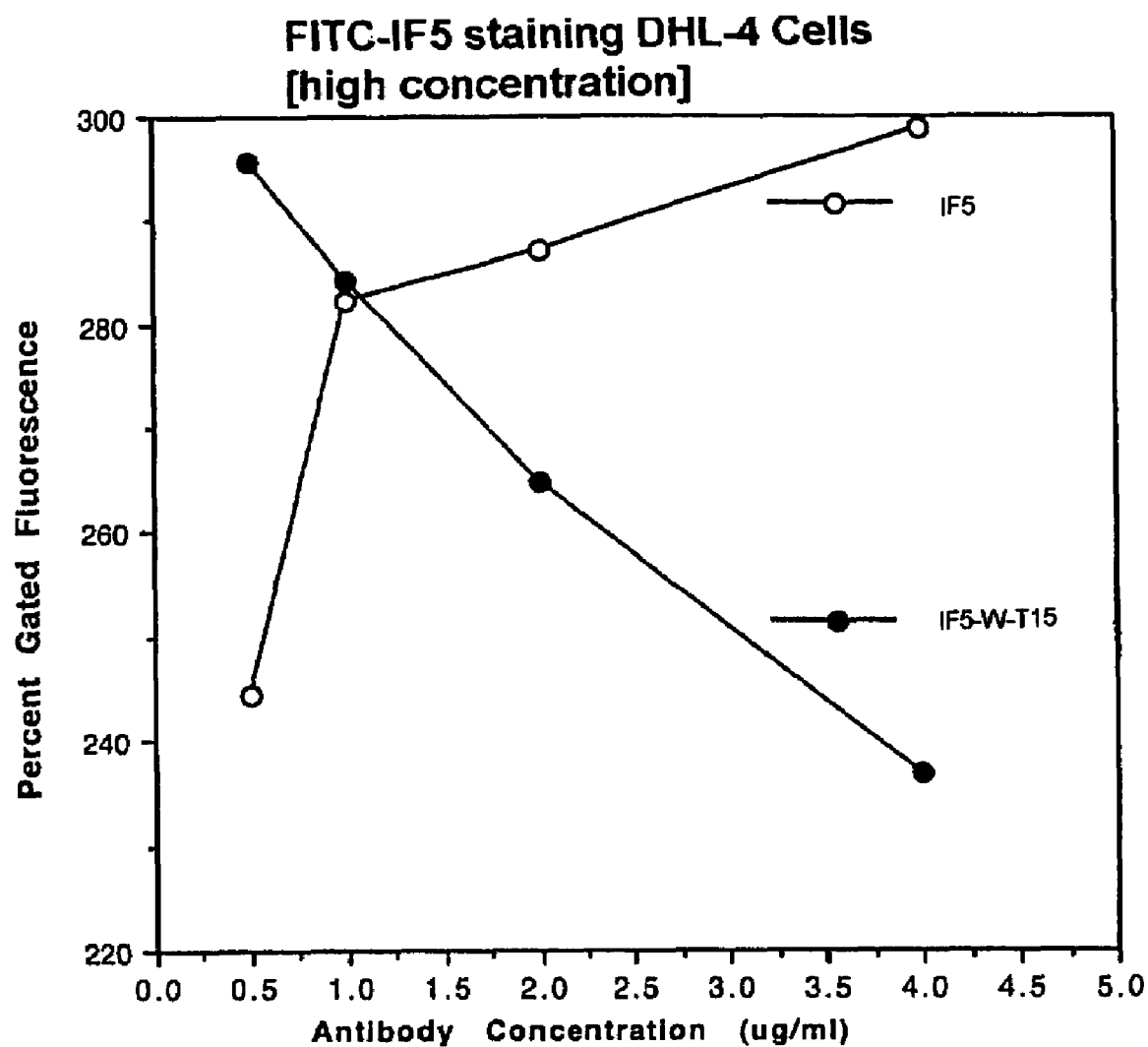
FIG. 1 is a graph depicting improved binding of anti-CD20 antibodies conjugated with T15 peptide to DHL-4 cells at high concentrations of antibody.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The present invention relates to non-covalent, autophilic antibodies having enhanced therapeutic potencies. Such antibodies are referred to as "autophilic" antibodies. Autophilic antibodies belong to the class of SuperAntibodies—antibodies that exhibit one or more properties not usually associated with antibodies (Kohler H., et al., 1998; Kohler H., 2000). The defined class of SuperAntibodies comprises catalytic, membrane-penetrating, and autophilic antibodies and includes many antibodies exhibiting superior targeting and therapeutic properties.

The autophilic antibodies of the present invention comprise antibodies conjugated with a peptide having an autophilic sequence. The autophilic antibodies of the invention can comprise any antibody. In some embodiments, the antibodies bind to targets implicated in a disease or disorder, where binding of the target has a therapeutic effect on the disease or disorder. The target antigens can include cell-surface antigens, including trans-membrane receptors. In specific embodiments, the antibodies comprise the monoclonal antibody 5D10, which binds human B-cell receptors, the monoclonal antibody S1C5, which binds murine B-cell receptors, anti-CD20 antibodies such as rituximab, which binds CD20 on normal and malignant pre-B and mature B lymphocytes, mouse monoclonal antibody IF5, which is specific for CD-20 on human B-cell lymphomas 5D10 and 3H1, and tositumab which also binds CD20 on B lymphocytes, anti-GM2, which binds human ganglioside GM2 lymphocytes, trastuzumab, which binds the protein HER2 that is produced by breast cells, anti-caspase antibodies, which recognize the caspase proteins involved in apoptosis, humanized TEPC-15 antibodies, which are capable of binding oxidized low density lipoproteins (oxLDL) and can prevent uptake of oxidized LDL by macrophages, humanized T15-idiotype positive antibodies, which bind phosphocholine, and humanized R24 antibodies which recognize the human GD3 ganglioside on melanoma cell surfaces.

The autophilic antibodies of the invention are conjugated with an autophilic peptide component. The autophilic peptide can comprise any autophilic peptide sequence. The autophilic peptide can also comprise optimized sequences which may include sequences with enhanced functionality, such as ones which act as linkers to enhance display and cross-linking activity of antibodies, or residues which enhance solubility of autophilic sequences. In all situations, the autophilic sequences are complementary and are able to bind to themselves.

In a specific embodiment, the autophilic peptide comprises the autophilic T15 peptide, which originally comprised regions of CDR2 and FR3 of the murine germline-encoded S107/TEPC15 antibody. The T15 peptide comprises amino acid sequence: ASRNKANDYTTDYSASVKGRFIVSR (SEQ ID NO.: 1) (Kang C-Y, et al., 1988). Its autophilic property has been shown to be antigen-independent. Therefore, attachment of the peptide to any monomeric antibodies can impart autophilic and increased avidity properties to the antibodies (Y. Zhao, and H. Kohler, 2002). In other specific embodiments, the autophilic peptide can comprise a humanized T15 peptide sequence, for increased or optimized binding and effectiveness of antibodies.

In other specific embodiments, the autophilic peptide can also comprise the peptide T15-scr2 comprising the sequence NH-SKAVSRFNAKGIRYSETNVDTYAS-COOH (SEQ ID NO. 4), the peptide R24 comprising the sequence NH-GAAVAYISSGGSSINYA-COOH (SEQ ID NO. 5), the peptide R24-Charged comprising the sequence NH-GKAVAYISSGGSSINYAE-COOH (SEQ ID NO. 6), and any modifications to the peptides which optimize or enhance the binding and therapeutic effectiveness of antibodies.

The autophilic antibody conjugates of the invention can also comprise one or more other bioactive or functional peptides which confer additional functionality on the antibody conjugates. For example, the antibody conjugate can comprise an antibody that bears a T15 autophilic peptide and an MTS membrane translocation peptide (Y. Zhao et al., 2003; Y. Lin et al., 1995). In a specific embodiment, the MTS translocation peptide can have the amino acid sequence KGEGAAVLLPVLLAAPG (SEQ ID NO. 2). In another embodiment, the translocation peptide can be an optimized MTS peptide, MTS-optimized, comprising the sequence WKGESAAVILPVLIASPG (SEQ ID NO. 7). The T15 peptide provides autophilicity to the conjugate, and the MTS sequence allows the antibody to penetrate into cells. Such a conjugate can target, for example, cancer cells for radio-immunotherapy, when its antibody region targets a primarily intracellular, tumor-associated antigen, such as carcino-embryonic antigen (CEA) (See, e.g., U.S. Pat. No. 6,238,667 which is hereby incorporated by reference). The autophilic conjugate, upon administration, targets CEA-bearing, colon carcinoma cells, is internalized by translocation of the antibody mediated by the MTS peptide, and is enabled to bind to the more prevalent intracellular form of CEA. Crosslinking of CEA antibody with, for instance, a therapeutic isotope such as $^{131}I$ will be retained in a cell longer than unmodified, labeled antibody and will deliver a higher radioactive dose to the tumor. In addition, such therapeutic isotopes as $^{125}I$, which release beta particles of short path length and are not normally considered useful for therapy, can, when delivered intracellularly in closer proximity to the nucleus, be efficacious against certain targets, especially those of lymphoid origin and accessible in the blood and lymph tissues. Other categories of secondary, bioactive or functional peptides include peptides capable of binding to receptors, and peptide mimetics, capable of binding to a distinctive antigen or epitope of the same antigen, targeted by the primary antigen combining site.

Autophilic antibodies conjugated with one or more other functional peptides may also be useful for targeting intracellular antigens. Such antigens could include tumour associated antigens and viral proteins. For example, an autophilic antibody specific for viral proteins which is conjugated with a self-binding peptide and a MTS peptide can also be used to bind to intracellular viral proteins and prevent production of viruses. The antibody could be internalized through the MTS peptide, and would be optimized to bind intracellular viral proteins (Zhao, Y., et al. 2003). Many other functional peptides may also be conjugated to the autophilic antibodies to increase functionality.

The invention also relates to compositions containing the autophilic antibodies of the invention and a pharmaceutically acceptable carrier. The conjugate autophilic antibodies can bind non-covalently with other autophilic antibodies when bound to their target antigen(s). However, premature formation of dimers or multimers of the antibodies may lead to difficulties in manufacturing, such as during purification and concentration, as well as drawbacks in administration, which may lead to side effects. As such, compositions containing the autophilic antibody-peptide conjugates of the invention are formulated to reduce this dimerizing potential and maximize monomericity while in solution and before administration. For example, it has been found that solution dimerization can be reduced or mitigated by using a hypertonic composition. In some embodiments, salt concentrations of 0.5M or more, low levels of SDS or other various detergents such as those of an anionic nature (see U.S. Pat. No. 5,151,266 which is hereby incorporated by reference), or modifications of the antibody to decrease its isoelectric point, for example through the use of succinyl anhydride (see U.S. Pat. No. 5,322,678, which is hereby incorporated by reference), can be used to formulate compositions.

According to the principles of the present invention, an autophilic antibody or a composition containing an autophilic antibody is preferably administered in one or more dosage amounts substantially identical to, or lower than, those practicable for unmodified antibodies. Thus, in the treatment of a lymphoma or a breast cancer, an autophilic antibody of the invention can be administered in one or more dose amounts substantially identical to, or less than, the doses used for RITUXAN™ (rituximab) or HERCEPTIN™ (trastuzumab). For example, treatment with HERCEPTIN™ (a humanized monoclonal anti-HER2/neu antibody) in a patient with HER2+ breast cancer employs an antibody concentration of about 10 mg/ml. Intravenous infusion over 90 minutes provides a total dose of 250 mg on day 0. Beginning at day 7, 100 mg is administered weekly for a total of 10 doses. The dosing regimen is reduced gradually from 250 mg to 100 mg to a maintenance dose of 50 mg. Similar or lower dosage regimens to that for HERCEPTIN™ can be employed with autophilic antibodies, with any adjustments being well within the capabilities of a skilled practitioner.

The present invention also relates to a method of producing the autophilic antibody conjugates. The antibody conjugates can be produced by chemical or genetic engineering techniques. For instance, a peptide component of an autophilic antibody can be attached to the immunoglobulin component via its variable domain structures using azido-tryptophan or azido-purine photoactivation crosslinking. In this approach, the peptide attaches to the variable domain at a location that does not interfere with antigen recognition. This method can incorporate two peptide moieties into a single immunoglobulin molecule. See, for example U.S. Pat. No. 6,238,667, U.S. Reissued Pat. No. RE38,008, U.S. Pat. Nos. 5,635,180, and 5,106,951, the disclosures of which are incorporated herein by reference.

The peptides can be photo-crosslinked to a heterocyclic compound affinity site (such as a tryptophane affinity site) or a nucleotide affinity site of antibodies to produce the autophilic antibodies of the invention. Alternatively, the peptides can be crosslinked to a carbohydrate site of the Fc portion or to an amino or sulfhydryl group of an antibody. In an alternative embodiment, the autophilic antibody can be conveniently expressed as a fusion protein of the autophilic peptide and whole immunoglobulin, or fragment thereof.

The present invention also contemplates a method of producing an autophilic conjugate of the invention in which a template peptide has been modified to enhance the crosslinking potential of the autophilic antibodies as described above. In one embodiment of the invention, such functionally enhanced peptides are determined by producing a series of synthetic peptides with substitutions at each amino acid position within the template sequence and then testing this library of peptides for autophilic binding or for binding to the original peptide sequence. Those peptides with superior binding to the original sequence are then conjugated to immunoglobulins and the resultant conjugates are tested for potency, specifity, and the unwanted ability to induce aggregation. In one specific embodiment, the T15 peptide sequence is altered and modified sequences are selected for enhanced function.

In other embodiments of the invention, the self-binding potential of a peptide can be enhanced by increasing complementarity of the sequence, such as described in U.S. Pat. No. 4,863,857 to Blalock et al., which is incorporated herein by reference. The self-binding potential of a peptide can also be enhanced by humanizing a self-binding peptide sequence which is derived from non-human animals. Humanizing a peptide sequence involves optimizing the sequence for expression or functionality in humans. Examples and methods of humanizing peptides and proteins have been previously described (Roque-Navarro et al., 2003; Caldas et al., 2003; Leger et al., 1997; Isaacs and Waldmann, 1994; Miles et al. 1989; Veeraraghavan et al., 2004; Dean et al., 2004; Hakenberg et al., 2003; Gonzales et al., 2004; and H. Schellekens, 2002).

An assay method is also contemplated that permits preselection of target antigens most suitable as targets for the autophilic antibodies of the present invention. Such method entails the in vitro assay of apoptosis with multiple antigen-positive target cell lines, and if possible, fresh isolates of antigen-positive cells. A non-modified antibody is incubated with a secondary (anti-immunoglobulin) antibody to enhance the potential for cross-linking. Cells may be enumerated by pre-labeling, such as with $^{51}$Cr or $^{131}$I-UDR, or by FACS analysis using indicators of apoptosis. Positive results in this assay predict a positive outcome using an autophilic conjugate. However, negative results in the assay do not necessarily mean that subsequent conjugation with an autophilic peptide will not improve one or more antibody effector properties.

Autophilic antibodies of the present invention have a higher potential for forming dimers in vitro under laboratory conditions, such as in solution with PEG. This laboratory characteristic correlates with a crosslinking ability upon binding to a cell-surface target and higher therapeutic potency through such mechanisms as triggering apoptosis. This characteristic can be used to identify natural SuperAntibodies and to screen for proper conjugation of self-binding peptides to a non-autophillic antibody.

A method of enhancing apoptosis, complement fixation, effector cell-mediated killing of targets, or preventing the development of, or enhancement of, a disease state, is also disclosed employing an autophilic conjugate of the invention or a composition comprising an autophilic conjugate of the invention. In one embodiment, an autophilic conjugate of the invention, or a composition containing an autophilic conjugate of the invention, is administered to a subject. Once administered, the antibodies bind to target cells and enhance apoptosis, complement fixation, effector cell-mediated killing of targets, or prevent target antigens or cells from stimulating the development of, or further enhancing, a disease state. In a further embodiment, allowing time for the autophilic conjugate to bind to target cells and enhance apoptosis, complement fixation, effector cell-mediated killing of targets, or prevent target antigens or cells from further enhancing a disease state, and for the autophilic conjugate to be cleared from normal tissues, a second anti-autophilic peptide antibody can be administered. For example, if an autophilic conjugate contains a non-native autophilic peptide, such as the murine T15 sequence, an anti-T15 peptide antibody would be administered, which would only recognize and bind to antibodies conjugated with the T15 sequence. This allows binding to and enhancement of apoptosis of pre-localized SuperAntibodies.

A further method of enhancing apoptosis, complement fixation, or effector cell-mediated killing of targets is contemplated, which employs administering an autophilic conjugate of the invention in which a template autophilic peptide has been modified to enhance the crosslinking potential of the autophilic antibodies as described above.

In another aspect of the invention, a method of potentiating apoptosis of targeted cells of a patient comprises administering a first autophilic antibody-peptide conjugate, or a composition containing an autophilic antibody-peptide conjugate, and a second antibody, or composition containing the second antibody, that recognizes the autophilic peptide domain of the conjugate. In this embodiment, the antibody-peptide conjugate recognizes an antigen on a target cell. Owing to its homodimerization property, the antibody-peptide conjugate can bind more avidly to the target than the corresponding antibody lacking the autophilic peptide domain. This is likely due to the ability to crosslink antigen at the surface of target cells. Moreover, whenever the autophilic antibodies bind to two or more antigens, with those antigens being brought in close proximity and crosslinked, due to the autophilic property of the antibodies, an apoptosis signal within the cell can be triggered. In those instances when the peptide domain of the conjugate presents an exposed epitope, a second antibody, specific for the autophilic peptide, can be administered, bind to the modified antibody, and enhance the process of crosslinking and even cause temporary clearance of the target antigen. As an example, if the target antigen is a receptor, clearance from the cell surface, endocytosis, and degradation will subsequently require synthesis of new receptor protein, meaning that the biological function of the receptor will be more effectively inhibited for a longer period than using either a simple blocking antibody or small molecule inhibitor. Alternatively, the second antibody can bear a radiolabel or other potentially therapeutic substance, so that when administered, it can attack the targeted cells. The key to use of this second antibody is the antibody's specificity. The autophilic peptide is present on only a small number of immunoglobulins, or if it is a peptide derived from another organism, or if it is modified, will not be present on any immunoglobulins in a patient. Thus, antibody specific to the autophilic peptide will have the requisite selectivity to be used in vivo.

In another aspect of the invention, a patient who suffers from a disease or condition responsive to antibody therapy is administered at least one autophilic antibody of the invention in an amount effective to alleviate symptoms of the disease or condition. A disease or condition contemplated for treatment by an antibody of the invention can be a malignancy, neoplasm, cancer, auto-immune disorder, Alzheimer's disease or other neuro-degenerative condition, graft or transplantation rejection, atherosclerosis, or any other disease or condition responsive to antibody therapy.

The following examples are presented to illustrate certain aspects of the invention, and are not intended to limit the scope of the invention.

EXAMPLES

Example 1

Conjugation of T15 Peptide to two Mabs Specific for B-cell Receptor

Cell Line and Antibodies.

The human B-cell tumor line (Su-DHL4) and murine B-cell tumor line (38C13) are grown in RPMI 1640 medium (supplemented with 10% fetal bovine serum, 2 µmol/L glutamine, 10 µmol/L HEPES, 50 U/mL penicillin, and 50 µg/mL streptomycin, 50 µmol/L 2-mercaptoethanol) at 37° C. under 5% carbon dioxide. Two mAb 5D10 and S1C5, specific for the human or murine BCR, respectively, were used in this study. The antibodies are purified from the culture supernatant by protein G and protein A affinity chromatography.

Synthesis of Antibody-Peptide Conjugate.

T15H peptide (ASRNKANDYTTDYSASVKGRFIVSR) (SEQ ID NO. 1), a VH-derived peptide from an autophilic antibody-T15, was synthesized by Genemed Synthesis (San Francisco, Calif., U.S.A.). Antibodies were dialyzed against PBS (pH 6.0) and 1/10 volume of 200 µmol/L sodium periodate was added and incubated at 4° C. for 30 minutes in the dark. The reaction was stopped by adding glycerol to 30 µmol/L, and the sample was dialyzed at 4° C. for 30 minutes against PBS (pH 7.0). One hundred times molecular excess of T15H or scrambled peptide was added to the antibodies and incubated at 37° C. for 1 hour. L-Lysine was added and incubated at 37° C. for 30 minutes to block the remained aldehyde group. The same oxidation reaction steps (except adding the peptides) were applied to antibodies used as controls. After the blocking step, the antibody conjugates were dialyzed against PBS (pH 7.2) overnight.

Ig Capture ELISA.

Four µg/mL of S1C5-T15H was coated to Costar vinyl assay plates (Costar, Cambridge, Mass.). After blocking with 3% BSA solution, 8 µg/mL of photobiotinylated S1C5-T15H, S1C5-scrambled peptide conjugate, and control S1C5 were added to the first wells, and 1:1 dilution was performed. The antibodies were incubated for 2 hours at room temperature. After washing with PBS buffer, Avidin-HRP (Sigma, St. Louis, Mo.) was added as a 1:2500 dilution. The binding antibodies were visualized by adding substrate o-phenylenediamine.

Size Exclusion Chromatography.

Antibody conjugate was chromatographed on a 75 mL Sephacryl 300HR column (Pharmacia, Peapack, N.J.). 1:10 diluted PBS (pH 7.2) was chosen as elution buffer. Fractions (0.5 mL/each) were collected and aliquots (100 µL) were assayed on antihuman IgG capture ELISA. The ELISA reading (OD 490 nm) is plotted against elution volume.

Viability Assay for Antibody-Treated Cells.

The lymphoma cells were grown in 96-well tissue culture wells in 1-mL medium. 2 µg of antibodies or antibody-peptide conjugates were added and incubated for various times as described herein. Ten µL aliquots from the cell suspension were used to determine viability by using trypan blue exclusion.

FACS Assay of the B-Cell Lymphoma.

The Su-DHL4 and 38C13 cells were fixed with 1% paraformaldehyde. $1\times10^6$ cells were suspended in 50 µL of staining buffer (Hank's balanced salt solution, containing 0.1% NaN3, 1.0% BSA), then 1.5 µg of photobiotinylated S1C5-T15H conjugates was added and incubated for 30 minutes on ice. Control antibodies and antibody-scrambled T15 peptide conjugates served as controls. The cells were washed twice with staining buffer before Avidin-FITC (Sigma) was added to the cells for 30 minutes on ice. Then the cells were washed twice with staining buffer, re-suspended in 200 µL PBS and analyzed by flow cytometry.

Hoechst-Merocyanin 540 Staining to Detect Apoptosis.

$1\times10^6$ of lymphoma cells were placed into 24-well tissue culture wells. Four µg of antibodies or antibody-peptide conjugates were added and incubated for various times as described herein. $1\times10^6$ cells were removed from the culture, re-suspended in 900 µL cold PBS (pH 7.2). One hundred µL of Hoechst 33342 (50 µg/mL; Molecular Probe, Eugene, Oreg., U.S.A.) was added, the cells were incubated at 37° C. for 30 minutes in the dark. The cells were centrifuged and re-suspended in 100 µL PBS. Then, 4 µL of MC540 solution (Molecular Probe) was added, and a 20-minute incubation was performed at room temperature in the dark. The cells were pelleted, re-suspended in 1 mL cold PBS (pH 7.2), and analyzed by flow cytometry.

RESULTS

Characterization of Autophilic Antibodies.

The T15H (24-mer) peptide was crosslinked to two murine mAb (S1C5 and 5D 10), using carbohydrate periodate conjugation. The mAb S1C5 (IgG1) is specific for the tumor idiotype of the mouse 38C13 B-cell line and the 5D10 antibody for the human Su-DHL4 B-cell tumor. Both antibodies recognize unique idiotypes of the BCR IgM on the B-cell tumors.

Autophilic Behavior can Easily be Demonstrated by ELISA.

The autophilic effect was studied with the T15H peptide-crosslinked mAb S1C15. The T15H-crosslinked S1C5 binds to insolubilized S1C5-T15H detected by biotin-avidin ELISA. Control S1C5 does not bind significantly to S1C5-T15H or S1C5 crosslinked with a scrambled peptide. Similar self-binding of T15H peptide-crosslinked mAb 5D10 to insolubilized T15H-5D10 was also observed. The specificity of the peptide mediated autophilic effect was tested using the 24-mer peptide T15H itself as an inhibitor. Only the T15H peptide inhibited S1C5-T15H and 5D10-T15H self-binding while the control-scrambled peptide did not inhibit it. These results are similar to the previously published inhibition data with the naturally occurring autophilic T15/S107 antibody (not shown).

T15H-Antibody Conjugates Form an Equilibrium of Monomer and Dimer in Solution.

The non-covalent nature of the self-aggregation of T15H-linked antibodies raises the question of its physical state in solution. To address this issue, the molecular species of T15H-linked monoclonal antibodies were analyzed using gel electrophoresis and sizing gel filtration. The electrophoretic mobility of control and T15H peptide conjugated to S1C5 and 5D 10 under reducing and non-reducing conditions show no differences, indicating the absence of chemical bonds between the antibody chains. The molecular species of the peptide-conjugated antibodies (5D10-T15H) was further analyzed by size exclusion chromatography. The elution profile indicated two immunoglobulin species of different sizes. The larger first peak eluted in the position of an antibody dimer. The second smaller peak eluted in the position of non-conjugated 5D10 antibody. The appearance of two peaks resembled monomer and dimer antibodies and could indicate that either a fraction of antibodies was not modified to polymerize, or that the modification was complete and the antibody establishes an equilibrium of dimers and monomers. To test the latter possibility, material from both peaks were subjected to a second gel filtration on the same column. Reruns of both peaks yielded again two peaks at the same position as in the first chromatography (Zhao and Kohler, 2002). These data show that the T15H peptide-linked antibodies exist in solution as two distinct molecular species in equilibrium as monomer and dimer.

Enhanced Binding of Autophilic Antibodies to Tumors.

The binding of the peptide-conjugated antibodies against their respective tumor targets was compared with that of the control antibodies in indirect fluorescence activated cell sorting (FACS). As control, antibodies linked with a scrambled peptide were included. The fluorescence intensity of the T15H-S1C5 on 38C13 cells is compared with that by the control S1C5 and the scrambled peptide S1C5. The difference in mean fluorescence channels between S1C5-T15H and controls was greater than 10-fold. Similarly, the FACS analysis of autophilic 5D 10-T15H on Su-DHL4 cells shows enhancement of binding over binding of control 5D10 and control peptide-crosslinked 5D 10. In both tumor systems, the conjugation of the T15H peptide to tumor-specific antibody enhanced the FACS signals over control antibodies used at the same concentration (Zhao, Lou, et al., 2002). The enhancement of fluorescence can be explained with the increase of targeting antibodies caused by self-aggregation and lattice formation on the surface of the tumor cells.

Inhibition of Tumor Growth.

Antibodies binding to the BCR induce crosslinking of the BCR, which, in turn, inhibits cell proliferation and produces a death signal. Furthermore, chemically dimerized antibodies directed against a B-cell tumor induce hyper-crosslinking of the BCR followed by inhibition of cell division and apoptosis of the tumor. To see if similar enhancement of the antitumor effects of dimerizing antibody were induced by our noncovalent, dimerizing T15H-linked antibodies, the two B cell tumors were cultured in the absence or presence of control and T15H-linked antibodies. Co-culture of both tumors, 38C13 and Su-DHL4, with their respective T15H-linked antibodies inhibited the cell growth significantly better compared with the control antibodies. To test the tumor target specificity of autophilic antibodies in growth inhibition, criss-cross experiments were performed with the 38C13 and Su-DHL-4 cell lines. Inhibition of 38C13 cell growth with S1C5-T15H was statistically greater than mismatched 5D10-T15H. Similar results on the specificity of autophilic antibodies were obtained with the Su-DHL4 cells (Zhao, Lou, et al., 2002).

Induction of Apoptosis.

As suggested by earlier studies, the antitumor effect of antibodies directed against the BCR of B-cell lymphomas in vitro and in vivo might be caused by the induction of apoptosis. Aliquots of tumor cells (38C13 and Su-DHL-4) cultured in the presence of control or T15H-linked antibodies were analyzed for apoptosis using a double stain FACS protocol. 38C13 and Su-DHL4 cells underwent a moderate amount of apoptosis without antibodies over a 6, respectively 18-hour culture. This apoptosis was enhanced when the respective antibody was added. However, when the T15H-linked antibodies were added, the accumulated number of apoptotic 38C13 cells was almost doubled, and apoptosis of Su-DHL4 cells was more than doubled during the entire culture (Zhao, Lou, et al., 2002).

The biologic advantage of the autophilic property is exemplified with the S107/T15 anti-phosphorylcholine antibody. This autophilic antibody is several times more potent in protecting immune-deficient mice against infection with *pneumococci pneumoniae* than non-autophilic antibodies with the same antigen specificity and affinity.

As shown here, the autophilic antibody function can be transferred to other antibodies by chemically crosslinking a peptide derived from the T15 VH germline sequence. The modified antibody mimics the autophilic property of the T15/S107 antibody, producing a autophillic antibody with increased avidity and enhanced targeting. Enhancing the binding of autophilic engineered antibodies to the BCR of B-cell tumor increases the strength of the death signals leading to profound inhibition of cell proliferation in culture. Even though the doubling of apoptosis is demonstrated here, other mechanisms of growth inhibition can be involved.

Crosslinking the BCR of the mature murine B-cell lymphoma A20 can protect against CD95 mediated apoptosis. This anti-apoptotic activity of engagement of the BCR by crosslinking antibodies is highly restricted to the time window of CD95 stimulation and is not dependent upon protein synthesis. The finding that BCR hypercrosslinking per se is pro-apoptotic is not at variance with reports on the anti-apoptotic activity of the BCR engagement, because it can be a result of the use of less mature B-cell lines in our study, to different strength of delivered signals by homodimerizing antibodies, or to Fas-independent apoptosis.

The use of two BCR idiotope-specific antibodies against different tumors offered the opportunity to test the biologic effect of targeting receptors other than the idiotope specific BCR. In criss-cross experiments with autophilic antibodies binding in FACS analysis and inhibition of growth in vitro show a significant enhancement only with the autophilic matched antibody. In this context, it is interesting to speculate whether enhanced tumor targeting would also augment cellular effector functions.

In an earlier study using chemically homodimerized antibodies, the Fc domain was not involved in the augmentation of growth inhibition and tumor cells lacking Fc receptors were susceptible to the antigrowth activity of homodimers. Thus, the anti-tumor effect induced by dimerizing antibodies would not be restricted to lymphoid tumors such as non-Hodgkin's B-cell lymphoma, where anti-tumor effects require the participation of Fc-receptor-bearing effector cells.

The described approach of transferring the naturally occurring autophilic property to other antibodies thereby enhancing their anti-tumor effect outlines a general method to improve the therapeutic efficacy of antibodies in passive immunotherapy.

Example 2

Internalization of Antibodies Conjugated with MTS Peptide

Cell line and antibodies

Human Jurkat T cells were grown in RPMI 1640 supplemented with 10% fetal bovine serum and antibiotic (penicillin, streptomycin and amphotericin). Rabbit polyclonal anti-active caspase-3 antibody (#9661 S) and anti cleaved-fodrin, i.e. alpha II spectrins (#2121 S) were purchased from Cell Signaling, Inc (Beverly, Mass.). Monoclonal (rabbit) anti-active caspase-3 antibody (#C92-605) was purchased from BD PharMingen (San Diego, Calif.). Mouse monoclonal antibody 3H1 (anti-CEA) was purified from cell-culture supernatant by protein G affinity chromatography. Anti-mouse and anti-rabbit HRP-conjugated secondary antibodies were purchased from Santa Cruz Biotechnologies, Inc. ApoAlert Caspase-3 Fluorescent Assay kit was purchased from Clonetech Laboratories (Palo Alto, Calif.). The Cell Death Detection ELISA was purchased from Roche Applied Science (Indianapolis, Ind.).

Synthesis of MTS peptide-antibody conjugate

MTS peptide (KGEGAAVLLPVLLAAPG) (SEQ ID NO. 2) was a signal peptide-based membrane translocation sequence, and synthesized by Genemed Synthesis (San Francisco, Calif.). Antibodies were dialyzed against PBS (pH 6.0) buffer, oxidized by adding 1/10 volume of 200 mmol/L NaIO4 and incubating at 4° C. for 30 min in the dark. Adding glycerol to a final concentration of 30 mM terminated the oxidation step. Samples were subsequently dialyzed at 4° C. for 1 h against 1×PBS (pH6.0) buffer. The MTS peptide (50 times molar excess) was added to couple the antibodies and the samples were incubated at 37° C. for 1 h and the resulting antibody-peptide conjugate was dialyzed against 1×PBS (pH 7.4).

Effect of MTS-conjugated antibody on cell growth

Jurkat cells ($2.5 \times 10^5$) were seeded into 96-well culture plate. After incubation with 0.5 μg MTS-antibody conjugates for 6, 12, 18 and 24 hour, aliquots were removed and viability was determined by trypan blue exclusion.

Study of antibody internalization by ELISA

Jurkat cells, grown in 1-ml medium in a 6-well culture plate, were incubated with 2 μg of unconjugated or MTS conjugated antibodies for 0, 1, 3, 6, 12 and 18 h. The cells were centrifuged and the culture supernatant was then transferred to a new tube. The cell pellet was washed twice with PBS (pH 7.4) before being homogenized by Pellet Pestle Motor (Kontes, Vineland, N.J.) for 30 sec. All of the cell homogenate and an equal volume of the culture (10 μl) supernatant were added to sheep anti-rabbit IgG coated ELISA plate (Falcon, Oxnard, Calif.) and incubated for 2 h at room temperature. After washing step, HRP-labeled goat anti-rabbit light chain antibody was added, and visualized using o-phenylenediamine.

DNA fragmentation

Jurkat cells were pre-treated with antibodies or a caspase-3 inhibitor (DEVD-fmk) for 1 h, centrifuged, and incubated with fresh medium containing actinomycin D alone (1 μg/ml) for 4 h. After treatment, Jurkat cells were collected, washed, and resuspended in 700 μl of HL buffer (10 mM Tris-HCl, pH 8.0, 1 mM EDTA, 0.2% Triton X-100,[4,11] for 15 min at room temperature. DNA was extracted with phenol:chloroform: isoamyl alcohol (25:24:1) and precipitated 24 h at −20° C. with 0.1 volume of 5 M NaCl and 1 volumes of isopropanol. The DNA was washed, dried, and resuspended in TE pH 8.0. The DNA was resolved by electrophoresis on a 1.5% agarose gel and visualized by UV fluorescence after staining with ethidium bromide. DNA fragmentation was also determined using the Cell Death Detection ELISA according to the manufacturer's instructions.

Preparation of total cell lysate

Jurkat cells were treated as described in the DNA fragmentation section. After treatment, cells were collected and washed with PBS (pH 7.4) twice, then suspended in 300 μl of CHAPS buffer (50 mM PIPES, pH 6.5, 2 mM EDTA, 0.1% CHAPS). The samples were sonicated for 10 sec and centrifuged at 14,000 rpm for 15 min at 4° C. The supernatant was transferred to a new tube and referred as total cell lysate.

Caspase-3-like cleavage activity assay

Jurkat cells were treated as described in the DNA fragmentation section. Equal amounts of protein of the total cell lysate was applied for caspase-3 activity assay using ApoAlert Caspase-3 Fluorescent Assay Kit according to the manufacturer's instruction. Fluorescence was measured with a Spectra MAX GEMINI Reader (Molecular Devices, Sunnyvale, Calif.).

Western blot analysis

Jurkat total cell lysates (10 ug) were separated on a 10% SDS-PAGE gel to detect immunoreactive protein against cleaved spectrin. Ponceau staining was used to monitor the uniformity of protein transfer onto the nitrocellulose membrane. The membrane was washed with distilled water to remove excess stain and blocked in Blotto (5% milk, 10 mm Tris-HCl [pH 8.0], 150 mM NaCl and 0.05% Tween 20) for 2 h at room temperature. Before adding the secondary antibody, the membrane was washed twice with TBST (10 mM Tris-HCl with 150 mM NaCl and 0.05% Tween 20), and then incubated with horseradish peroxidase-conjugated secondary antibodies. The blot was washed extensively and reactivity was visualized by enhanced chemiluminescence (AmershamBiotech, Piscataway, N.J.).

Statistical analysis

Statistical analysis was performed using the student t-test (for a pair-wise comparison) and one-way ANOVA followed by Newman-Keuls posttest. Data are reported as means±SE.

Results

Figure 7:
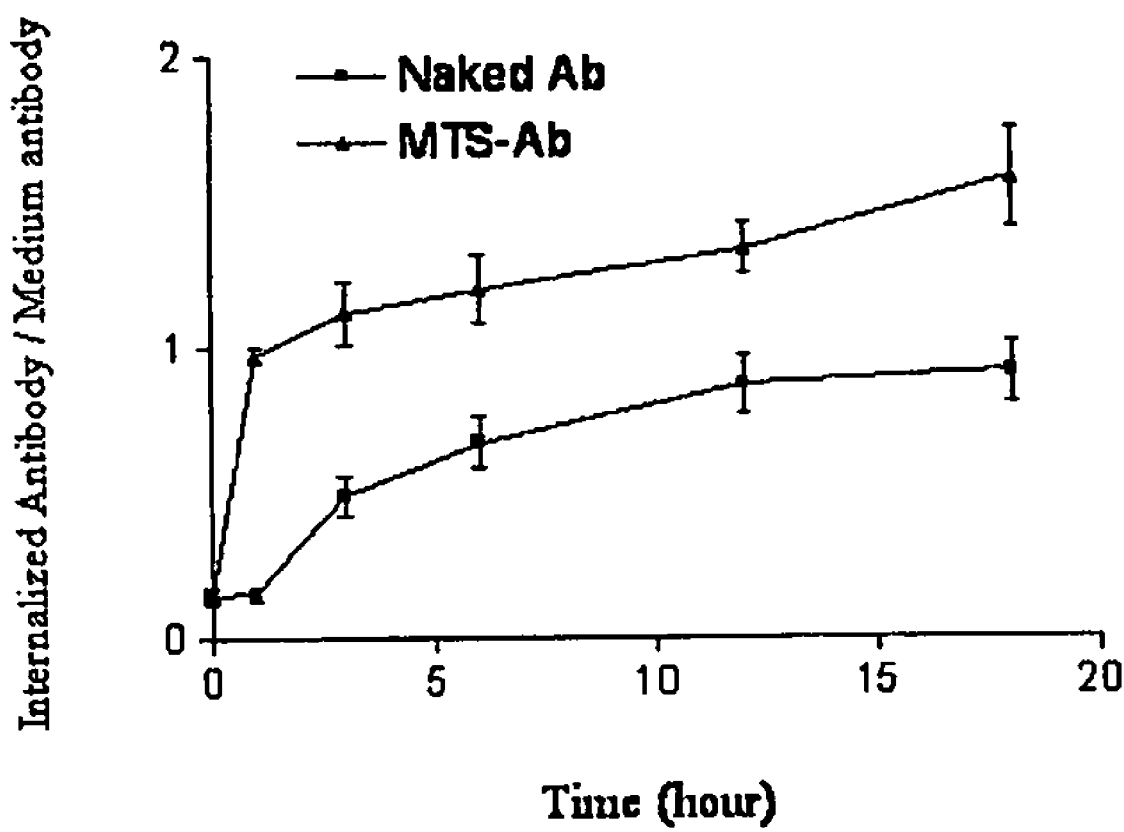
FIG. 7 is a graph comparing the internalization of MTS conjugated antibodies and non-MTS conjugated antibodies using anti-caspase 3 antibodies.
Figure 14:
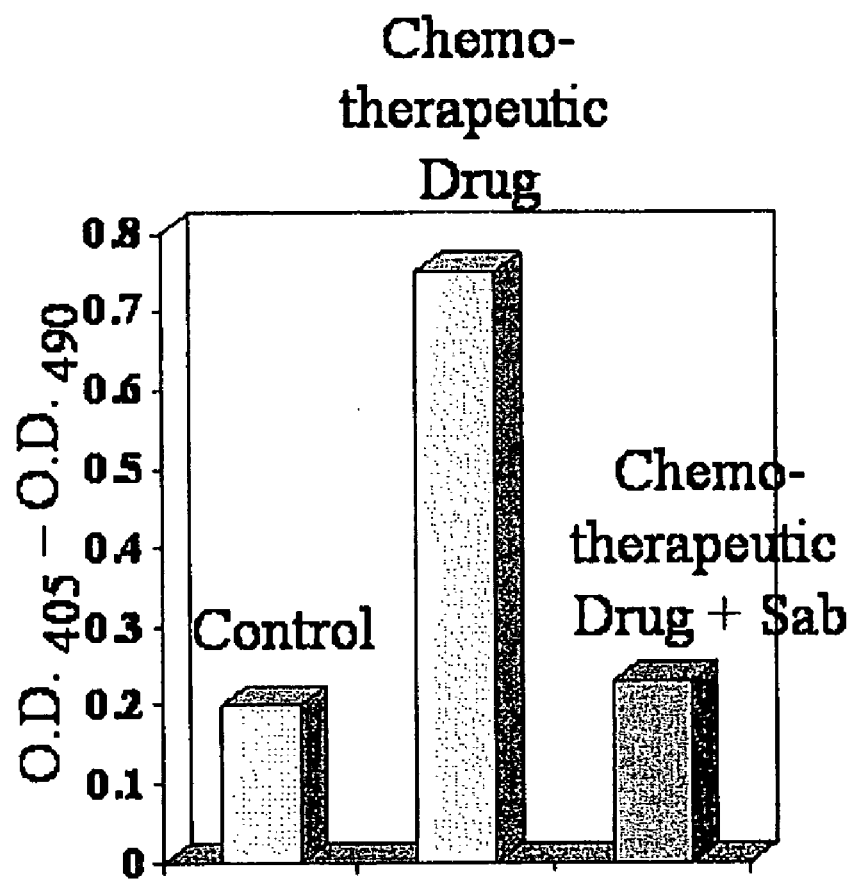
FIG. 14 is a graph depicting the effect of chemotherapeutic drug (actinomycin D) on cell death in the presence and absence of MTS-conjugated (Sab) antibody.

As shown in FIG. 7, an MTS conjugated anti-active caspase 3 antibody is internalized more rapidly than unmodified antibody. When cells were exposed to the chemotherapeutic drug, actinomycin D, apoptosis was triggered and the cells died (see FIG. 14). However, if cells were exposed at the same time to the MTS conjugated antibody (transMab), most of the toxicity of the chemotherapeutic drug was inhibited.

Example 3

Enhancing Binding and Apoptosis Using Peptide-Conjugated Anti-CD20 Antibodies

Materials and Methods

Cell Line and Antibodies

The human B-cell tumor lines SU-DHL-4 and Raj were grown in RPMI 1640 medium, supplemented with 10% fetal bovine serum, 2 mmol/L glutamine, 10 μmol/L Hepes, 50 U/mL penicillin, 50 μg/mL streptomycin, and 50 μmol/L 2-mercaptoethanol at 37° C. under 5% CO2. Mouse monoclonal antibodies 1F5 IgG2a (ATTC #HB-9645) specific for human B-cell lymphomas 5D10 and 3H1 (Zhao, Lou, et al., 2002.) were purified from cell culture supernatant by protein G or protein A affinity chromatography.

Synthesis of Antibody-Peptide Conjugate

T15 peptide (ASRNKANDYTTDYSASVKGRFIVSR) (SEQ ID NO. 1), a VH-derived peptide from a self-binding antibody-T15, was synthesized by Genemed Synthesis, California. The antibodies were dialyzed against phosphate-buffered saline (PBS; pH 6.0) buffer; sodium periodide (1:10 volume of 200 μmol/L NaIO4) was added; and the mixture was incubated at 4° C. for 30 minutes in the dark. The oxidation was stopped by adding glycerol (30 μmol, final concentration), and dialysis was performed at 4° C. for 30 minutes against PBS (pH 7.0) buffer. One hundred times molecular excess of T15 peptide was coupled to the antibody 1F5 by incubation at 37° C. for 1 hour; 1-lysine was used to block the unreacted aldehyde by incubation at 37° C. for 30 minutes. After the blocking step, the antibody conjugates were dialyzed against PBS (pH 7.2) overnight.

8-azido-adenosine-biotin was synthesized and used to affinity cross-link biotin to antibodies. The 8-azidoadenosine dialdehyde was prepared as previously published (U.S. Pat.

No. 5,800,991 for "Nucleotide or nucleoside photoaffinity compound modified antibodies, methods for their manufacture and use thereof as diagnostics and therapeutics," issued to Haley et al., 1998, which is incorporated herein by reference)

Self-Binding Enzyme-Linked Immunosorbent Assay

Four micrograms per milliliter of 1F5-T15 was used to coat Costar vinyl assay plates (Costar, Cambridge, Mass., U.S.A.). After blocking with 1% (BSA) solution, 8 ug/mL photobiotinylated (see U.S. Pat. No. 5,800,991 discussed above) 1F5-T15 naked 1F5 and control antibody (5D10) were added, diluted to 1:1, and incubated for 2 hours at room temperature. After washing with PBS buffer, avidin-HRP (Sigma, St. Louis, Mo., U.S.A.) was added, and enzyme-linked immunosorbent assay color was developed with o-phenylenediamine.

FACS Assay of the B-Cell Lymphoma

SU-DHL-4 cells were fixed using 1% paraformaldehyde, and 1×10⁶ cells were suspended in 50 µL staining buffer (Hanks, containing 0.1% NaN3 and 1.0% BSA); 1.5 µg photobiotinylated 1F5-T15 conjugates (see U.S. Pat. No. 5,800,991 discussed above), naked 1F5, and control antibodies were added and incubated for 30 minutes on ice. The cells were washed twice with staining buffer, and then avidin-FITC was added for 30 minutes on ice. After washing twice with staining buffer, the cells were resuspended in 200 µL PBS for FACS analysis.

Hoechst-Merocyanin 540 Staining to Detect Apoptosis

After 1×10⁶ lymphoma cells were placed into 24-well tissue culture wells, 4 µg antibodies and antibody-peptide conjugates were added. After 24 hours of incubation, 1×10⁶ cells were removed from the culture pellet and resuspended in 900 µL cold PBS (pH 7.2), and 100 µL Hoechst (Pierce, Rockford, Ill., U.S.A.) 33342 (50 µg/mL) was added and incubated at 37° C. for 30 minutes in the dark. The cells were centrifuged and resuspended in 100 µL PBS; 4 µL MC540 dilution solution was added and the cells were incubated for 20 minutes at room temperature in the dark. The cells were pelleted, resuspended in 1 mL PBS, and analyzed by flow cytometry.

Inhibition of Cell Growth in Culture

One×10⁵ tumor cells were seeded in complete culture medium. At days 1, 2, and 3 of culture, aliquots were removed and viable cells were counted using dye exclusion (trypan blue).

Results

Figure 2:
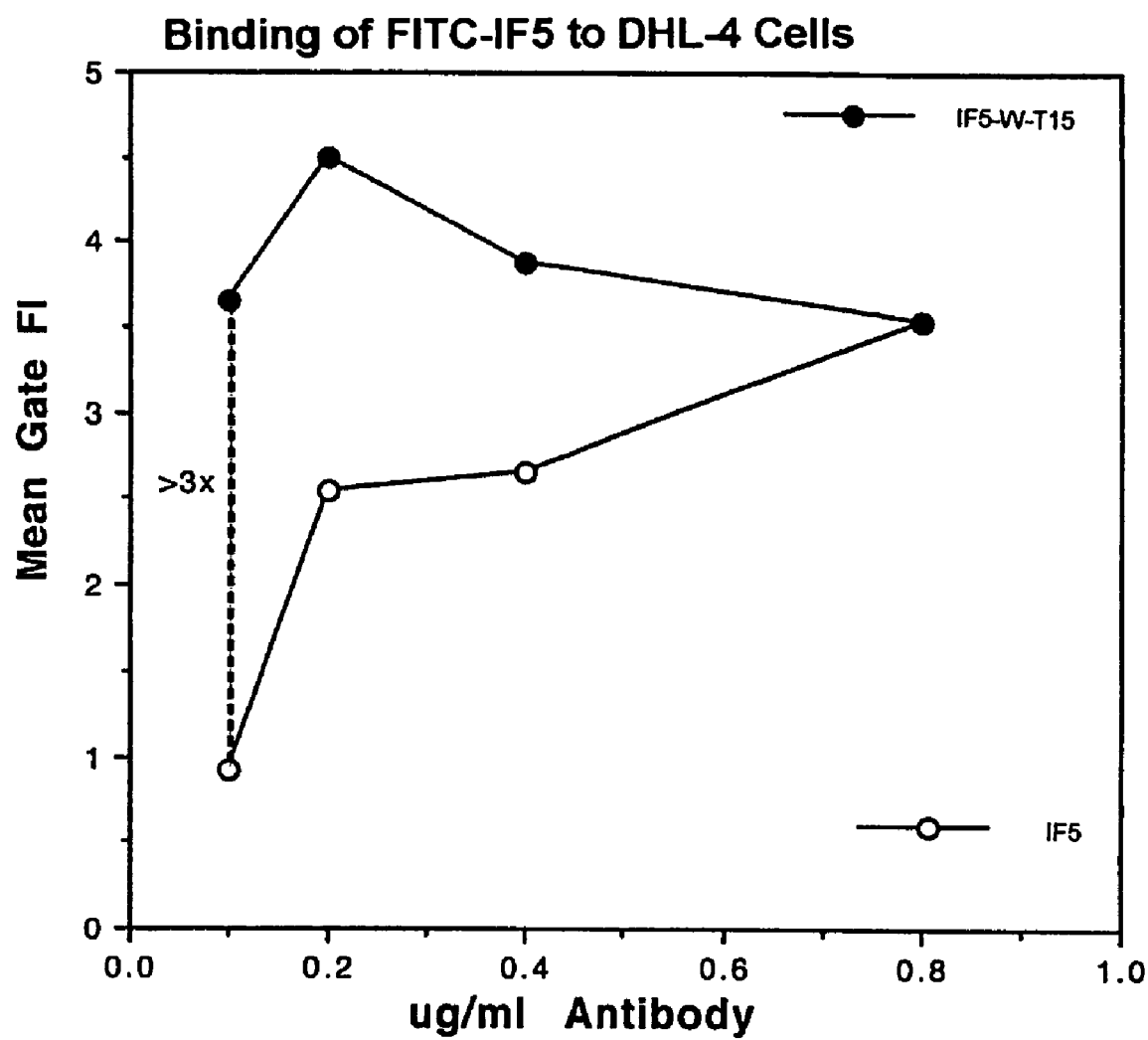
FIG. 2 is a graph depicting improved binding of anti-CD20 antibodies conjugated with T15 peptide at low concentrations of antibody.
Figure 3:
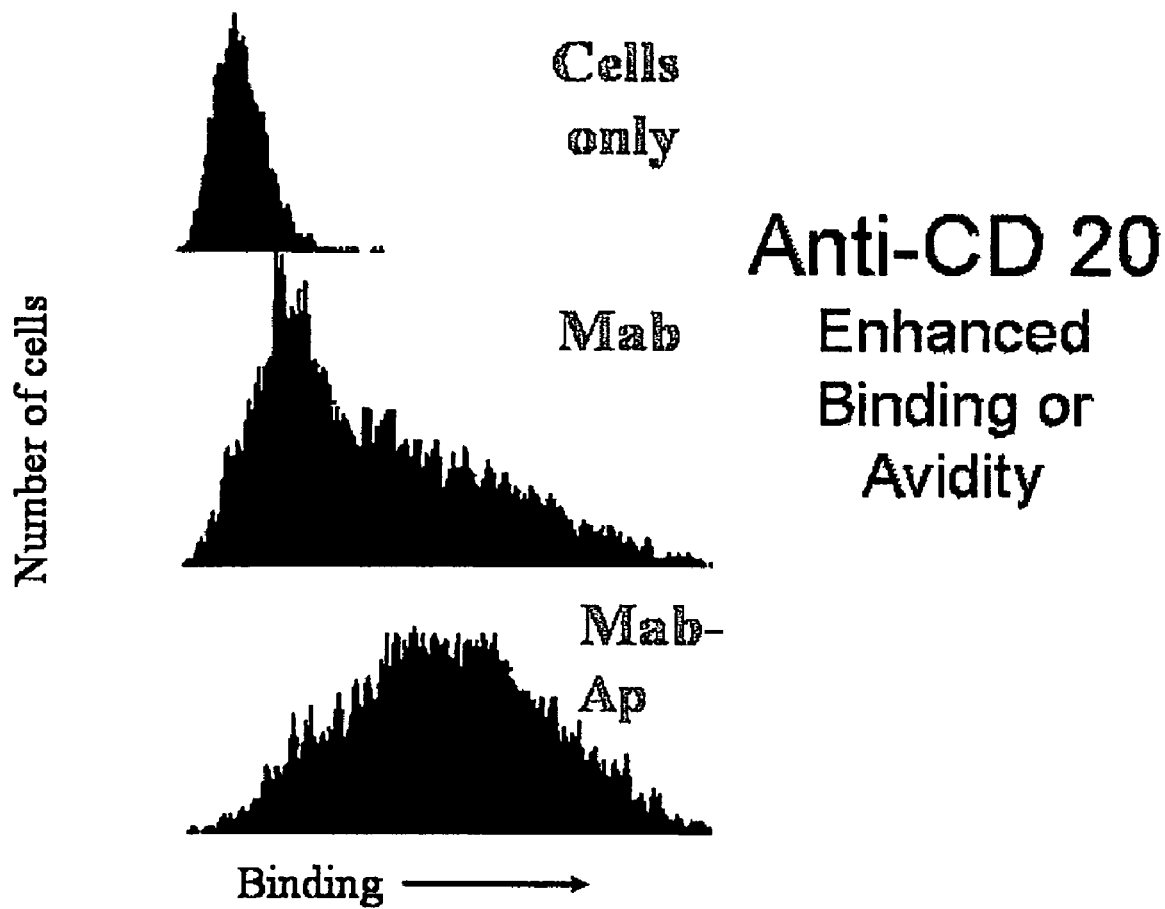
FIG. 3 is a graph depicting enhanced binding of anti-CD20 antibodies conjugated with T15 peptide.
Figure 4:
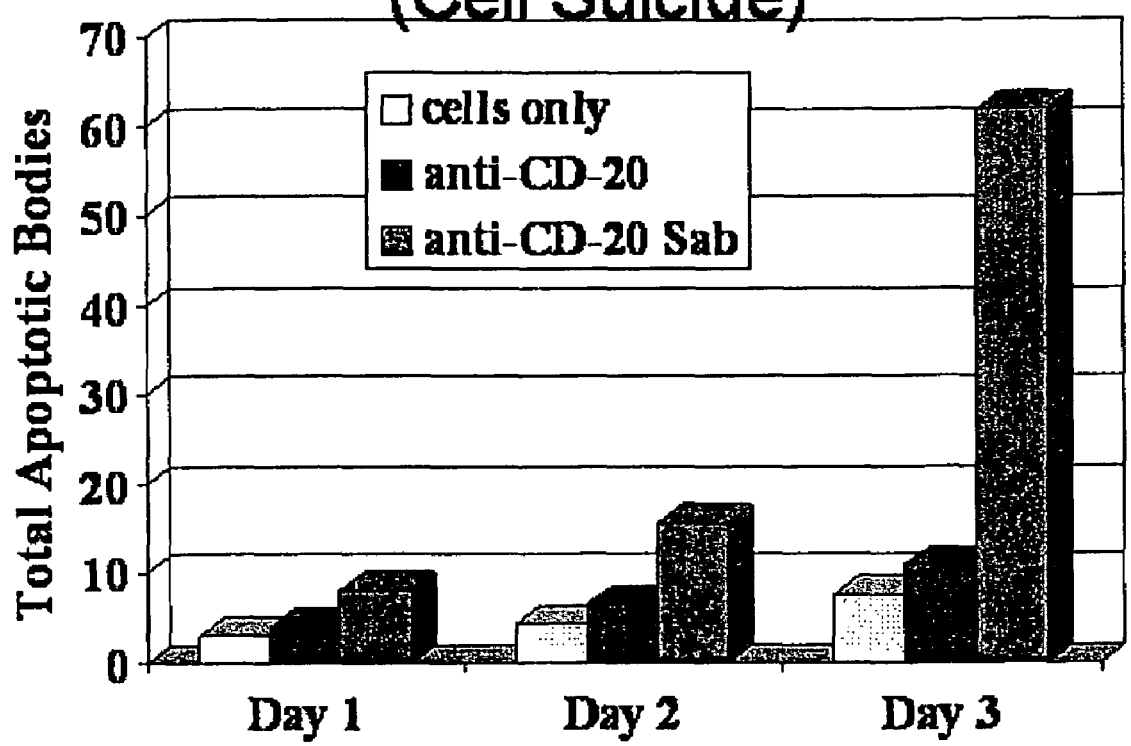
FIG. 4 is a graph depicting enhanced induction of apoptosis of tumor cells with mouse anti-CD20 conjugated with T15 peptide.

Mouse monoclonal antibodies 1F5 IgG2a were conjugated with self-binding peptide as in Example 1. An average of 1.8 peptides were found by competitive analysis. The parental antibody was compared to the conjugated form for binding by flow cytometry. As shown in FIG. 3 the binding was increased for the conjugated antibody (Mab-ap) when assessed with a limiting dilution of antibody. This was characterized by a shift in the binding fluorescence to a higher intensity. When compared over a series of dilutions, conjugated antibody required almost one-tenth the concentration of antibody to achieve the same level of intensity as parental antibody (FIG. 2). As shown in FIG. 1, increasing the amount of conjugated antibody caused a reduction in fluorescence intensity, presumably due to internalization, a property of SAT technology that can be used to enhance potency of immunoconjugates of drugs, toxins and short path length radiotherapeutic isotopes. Furthermore, when tested for the ability to trigger apoptosis, the conjugated form (Sab) was much more active than native antibody, with most cells dead by 3 days, compared to only a small fraction with the native antibody (see FIG. 4).

Example 4

Enhanced Binding and Apoptosis with Anti-GM2 Antibodies

Materials and Methods

Cell lines and antibody

Human T-cell leukemia Jurkat cells were grown in RPMI 1640 supplemented with 10% fetal bovine serum and antibiotic (penicillin, streptomycin and amphotericin). Chimeric hamster anti-GM2 antibody (ch-α-GM2) was obtained from Corixa Corporation (Seattle, Wash.). After chimerization, the resulting antibody lost its ability to induce apoptosis in ganglioside GM2 expressing target cells.

Synthesis of antibody-peptide conjugate

Both the T15 peptide (GAAASRNKANDYTTEYSASVKGRFIVSR) (SEQ ID NO. 8), a VH-derived peptide from a self-binding antibody-T15 (Kaveri et al, 1991), and a scrambled peptide (T15-scr) (SEQ. ID. NO. 3), which was randomly generated using the T15 amino acid sequence, were synthesized by Genemed Synthesis (South San Francisco, Calif.). The scrambled peptide was used as a control. Antibodies were dialyzed against PBS (pH 6.0), then {fraction (1/10)} volume of 200 µM NaIO4 was added and incubated at 4° C. for 30 min in the dark. The reaction was stopped by adding glycerol to a final concentration of 30 µM, and the samples were dialyzed at 4° C. for 30 min against PBS (pH 6.0). Fifty (50) times molecular excess of T15 or scrambled peptide was added to the antibodies and incubated at 37° C. for 1 h. L-Lysine was added and incubated at 37° C. for 30 min to block the remaining reactive aldehyde group. After the blocking step, the antibody-conjugates were dialyzed against PBS (pH 7.2) at 4° C. overnight, then stored at 4° C. until used.

Direct binding ELISA

GM2 ganglioside was dissolved in methanol and 0.5 µg was coated per well in 96 well polystyrene plates (Costar, Cambridge, Mass.) and allowed to dry overnight. The wells were blocked with 1% BSA for 2 h at room temperature and 400 µg of anti-GM2 antibodies, diluted in 1% BSA, were added in the first well and then serially diluted 1:1. After incubation for 1 h, the wells were washed 5× and HRP-conjugated anti-human IgG (Sigma, St. Louis, Mo.) was added at a 1:1000 dilution and incubated for 1.5 h. After washing three times, the bound antibodies were visualized using substrate o-phenylenediamine and read at OD 492 using a spectrophotometer.

Specific binding ELISA

Gangliosides GM2, GM1, GM3 were dissolved in DMSO in 0.5 µg and coated in 96 well polystyrene plate (Costar, Cambridge, Mass.) dried over night. The wells were blocked with 1% BSA for 2 h at room temperature, 400 µg of ch-α-GM2 antibodies (anti-GM2-T 15) were added in the first well and then serially diluted 1:1. After incubation for 1 h, the wells were washed 5× and HRP-conjugated anti-human IgG (Sigma, St. Louis, Mo.) was added and incubated for 1.5 h. After washing three times, the bound antibodies were visualized using substrate o-phenylenediamine and assayed as described previously.

Antibody self-binding ELISA

2 µg/ml of naked ch-α-GM2 (anti-GM2) or ch-α-GM2-T15 (anti-GM2-T15) were coated onto Costar vinyl assay plates. After blocking with 3% BSA solution, 0.5 µg/well of photobiotinylated anti-GM2-T15 was added. The antibodies were then incubated for 2 h at room temperature. After washing three times, avidin-HRP (Sigma) was added at a 1:1000 dilution and incubated for 1 hour. The bound antibodies were visualized by adding substrate o-phenylenediamine and assayed as described previously.

Cell Surface binding detected by FACS

Two×$10^5$ Jurkat cells per well were seeded in a 6-well plate and incubated overnight, then cells were collected and washed twice with P/B/G/A buffer (0.5% BSA, 5% Goat Serum in PBS). Cells were then resuspended in 100 µl P/B/G/A buffer containing 5 µg/ml anti-GM2 antibodies for 30 min. After washing with P/B/G/A buffer, FITC-conjugated anti-Human IgG (Sigma, 1:1000 dilution in 100 µl P/B/G/A) was added and incubated on ice for 30 min. After washing with P/B/G/A buffer, cells were resuspended in 400 µl P/B/G/A containing 10 µg/ml propidium iodide (as viability probe) and analyzed by flow cytometry.

Apoptosis detected by Annexin V staining

2×$10^5$ Jurkat cells were seeded per well in a 6-well plate. After 6 h, cells were incubated with 20 µg/ml of the anti-GM2 or anti-GM2-T15 antibodies for 12 hr. Following the incubation, a small portion of cells (50 µl) was saved and assayed for viability, while the remainder of the cells were harvested and washed with cold PBS. Cells were then resuspended in 100 µl annexin staining buffer (5 µl Alex fluor 488 was added into 95 µl 1×annexin binding buffer, and Sytox was added at a dilution of 1:1000. After incubation at room temp for 15 min, 400 µl of 1×annexin binding buffer was then added, and samples were analyzed by FACS.

Viability assay for Antibody-treated cells

A small portion of the cell samples saved from the annexin experiment was used for viability assay. 10-µl aliquots from the cell suspension were taken to determine viability using trypan blue exclusion assay.

Statistical analysis.

Statistical analysis was performed using one-way ANOVA followed by Newman-Keuls post test. Data are reported as means+SD.

Results

Self-binding peptide enhanced antibody binding to its specific ganglioside.

Figure 9:
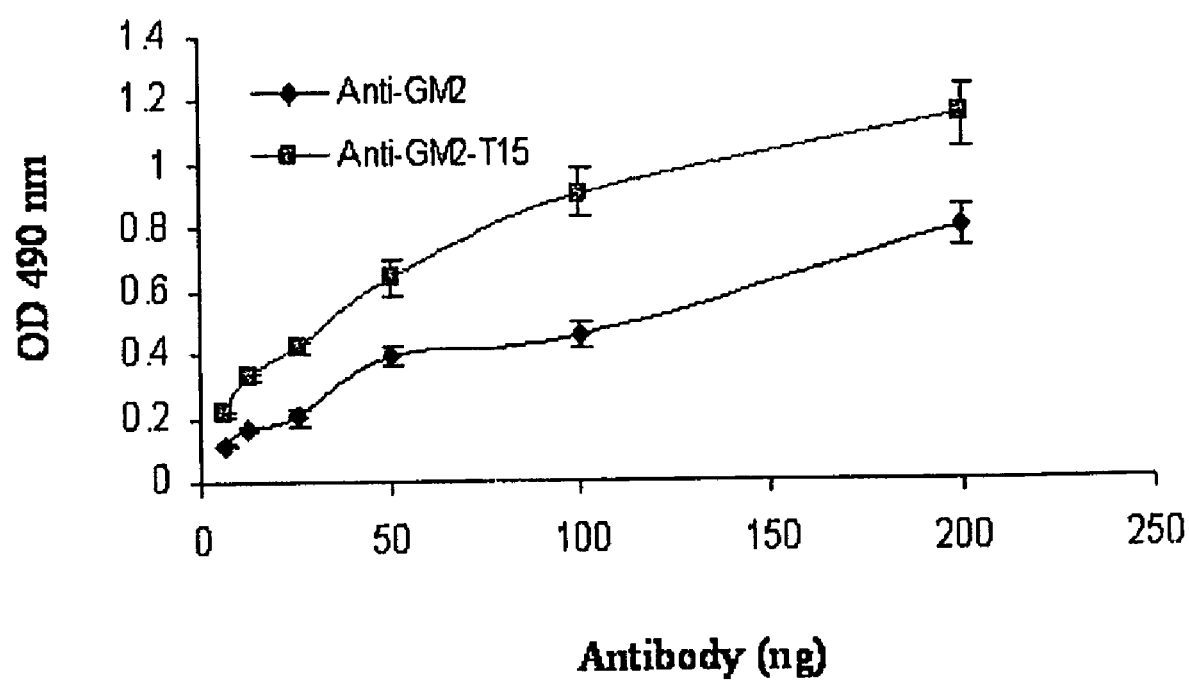
FIG. 9 is a graph comparing the binding of anti-GM2 antibody and T15 conjugated anti-GM2 antibody to ganglioside GM2.

Following antibody-peptide conjugation, the binding capacity of the T15-conjugated ch-α-GM2 antibody (anti-GM2-T15) was determined using a direct binding ELISA. As seen in FIG. 9, both ch-α-GM2 antibody (anti-GM2) and anti-GM2-T15 antibody showed a dose-dependent increase in binding to ganglioside GM2. The anti-GM2-T15 antibody demonstrated a higher binding capacity compared with the naked anti-GM2 at all the doses tested, confirming that the self-binding T15 peptide had increased the antigen binding capacity of the ch-α-GM2 antibody at a given antibody concentration.

Antibody self-binding behavior demonstrated by ELISA

Figure 10:
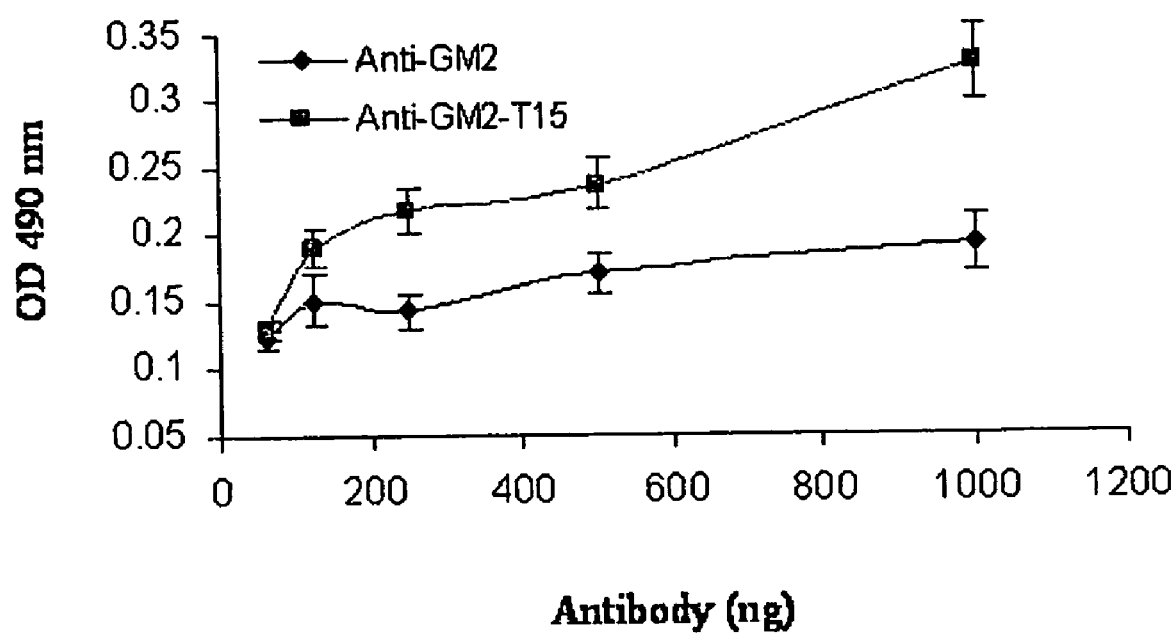
FIG. 10 is a graph illustrating the self-binding activity of anti-GM2 antibody and T15 conjugated anti-GM2 antibody.

Next, it was investigated by ELISA whether the increase in binding to ganglioside GM2 by the T15 peptide-linked antibody was due to its self-binding feature. As seen in FIG. 10, the anti-GM2-T 15 antibody demonstrated a greater dose-dependent increase in binding to the peptide-conjugated anti-GM2-T15 antibody coated on the wells, whereas it did not show significant binding to the non-peptide conjugated anti-GM2 antibody. These data demonstrate that the anti-GM2-T15 antibody can bind to itself or homodimerize through the Fc-conjugated, autophilic peptide moiety.

T15 conjugation does not change the specificity of the ch-α-GM2 antibody.

Figure 11:
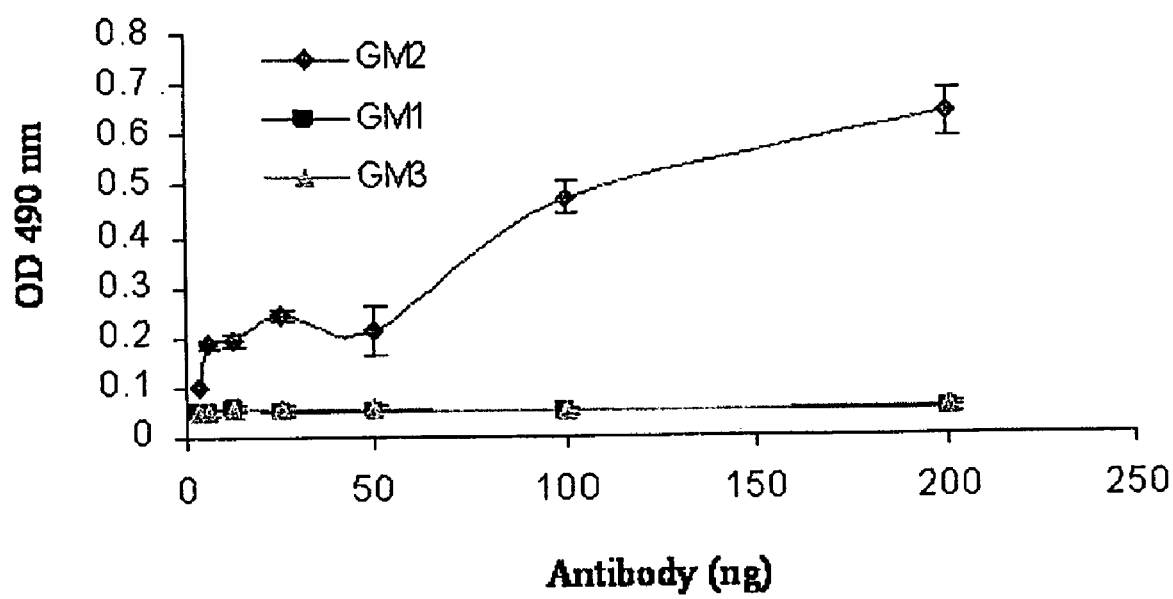
FIG. 11 is a graph demonstrating binding specificity of T15 conjugated anti-GM2 antibody to different gangliosides.

To assess whether conjugation of the T15 peptide might alter the cognate binding specificity of the antibody, a direct antigen-binding ELISA was used to determine the binding specificity of the anti-GM2-T15 conjugated antibody. As shown in FIG. 11, the anti-GM2-T15 antibody demonstrated a specific, dose-dependent increase in binding to ganglioside GM2, whereas no binding above background levels to gangliosides GM1 or GM3 was detected. This result confirms that addition of the self-binding T15 peptide did not alter nor reduce the specificity of the ch-α-GM2 antibody.

Enhanced surface binding of anti-GM2 antibody to target tumor cells

Figure 12:
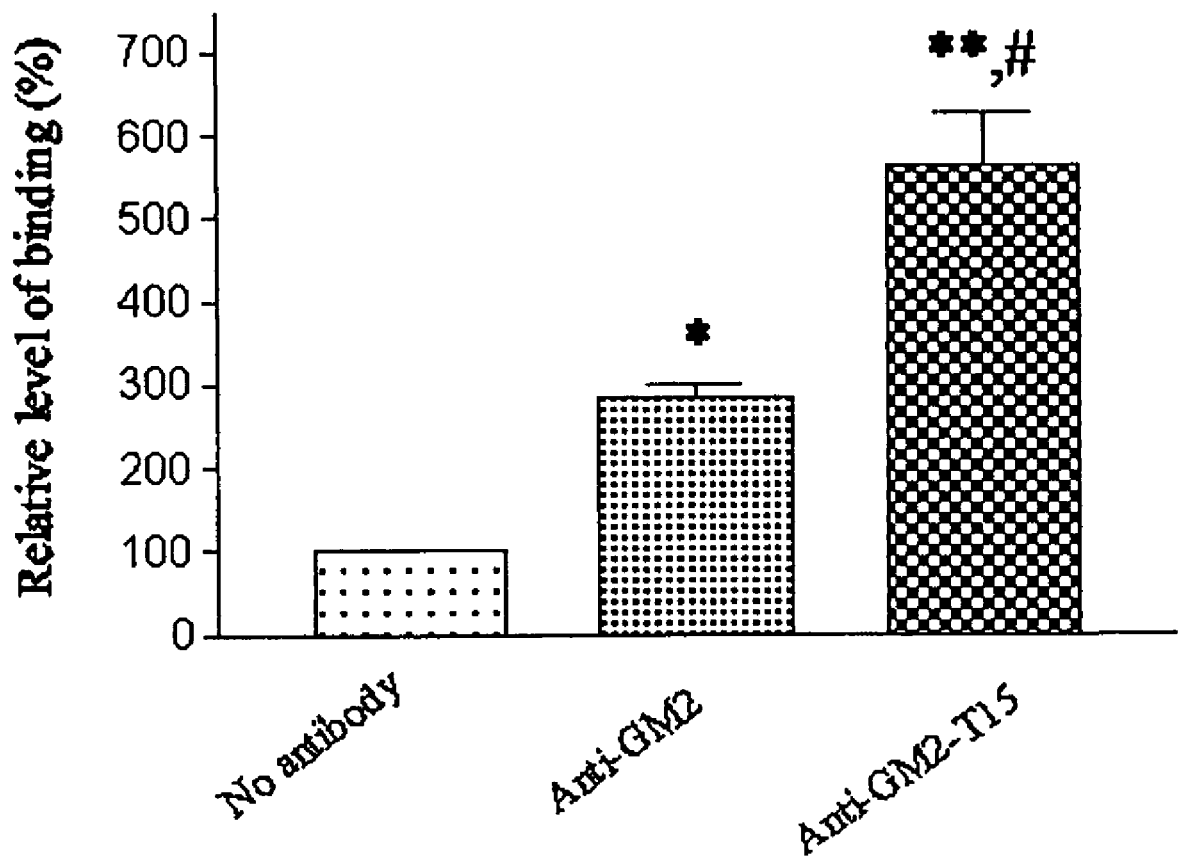
FIG. 12 is a graph depicting differences in cell surface binding of anti-GM2 antibody and T15 conjugated anti-GM2 antibody to Jurkat cells.

The human T-cell leukemic cell line Jurkat is known to express ganglioside GM2 (Suzuki et al, 1987). The ability of the peptide-conjugated anti-GM2-T15 antibody to bind to native ganglioside GM2 expressed on the surface of Jurkat cells was compared to that of the non-conjugated anti-GM2 antibody by flow cytometry. As shown in FIG. 12, the ch-α-GM2 antibody (anti-GM2) demonstrated a GM2 specific binding signal 3 times greater than background levels, whereas the binding demonstrated by the T15-conjugated anti-GM2 antibody was 2-fold higher than that of the non-peptide conjugated antibody. This result suggests that the enhanced binding demonstrated by the peptide-conjugated Ab is due to self-aggregation of this antibody.

Inhibition of tumor growth

Figure 13:
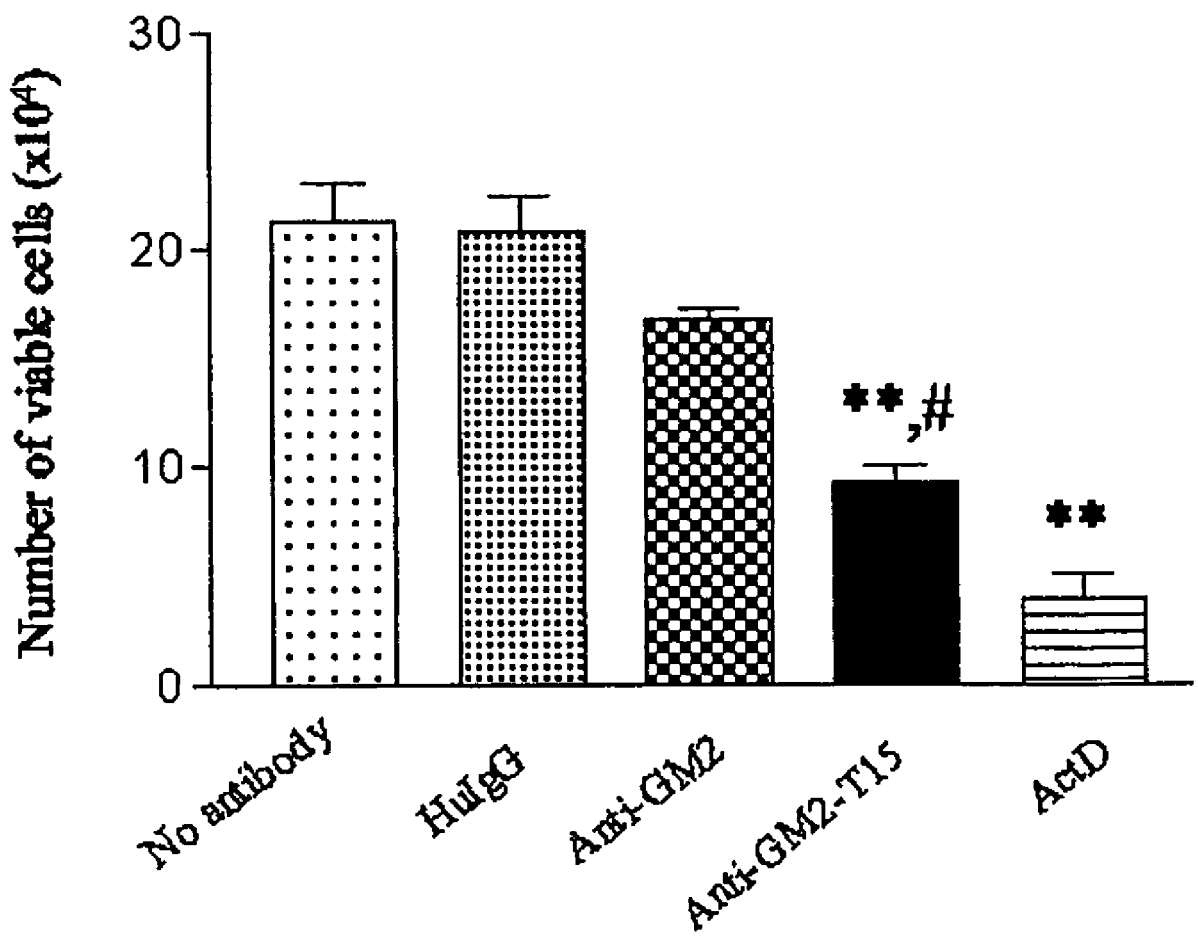
FIG. 13 is a graph depicting the effect of anti-GM2 antibody and T15 conjugated anti-GM2 antibody on Jurkat cell growth.

Antibodies binding to the B cell receptor have been shown to induce crosslinking of the BCR, which, in turn, inhibits cell proliferation (Ward et al, 1988) and produces a death signal (Hasbold et al, 1990; Wallen-Ohman et al, 1993). Furthermore, chemically dimerized antibodies directed against a B-cell tumor induce hyper-crosslinking of the BCR followed by inhibition of cell division and induction of apoptosis of the tumor cells (Ghetie et al, 1994; Ghetie et al, 1997). To determine whether the T15-conjugated anti-GM2 antibody induced a similar anti-proliferative effect, 2×$10^5$ Jurkat cells were cultured in the presence or absence of anti-GM2 or control antibodies for 12 h, and then the number of viable cells remaining were counted. As summarized in FIG. 13, no antibody or control human IgG antibody (HuIgG) treatment had no effect on cell growth or viability, whereas there was some effect with the anti-GM2 antibody. However, the T15-linked antibody demonstrated a marked inhibition of Jurkat cell growth, as cell numbers were reduced >2-fold compared to naked anti-GM2 antibody treated cells, and more than 4 fold versus the control IgG treatment. As a comparison and positive control, Actinomycin D demonstrated the ability to induce apoptosis, at levels slightly higher than the SuperAntibody.

Induction of Apoptosis

In order to determine whether the anti-tumor effect of antibodies directed against cell surface expressed gangliosides might be due to the induction of apoptosis, we took the cell samples used in the cell growth study and analyzed them for apoptosis induction by measuring annexin V staining. The results are summarized in Table 1.

TABLE 1

| Apoptosis analysis using Annexin V staining. | |
|---|---|
| Antibody | Jurkat* |
| No treatment | 7.7 ± 1.55 |
| HuIgG | 7.2 ± 1.94 |
| Anti-GM2 | 14.8 ± 7.55 |
| Anti-GM2-T15scr | 13.0 ± 4.60 |
| Anti-GM2-T15 | 54.2 ± 23.4 |
| Actinomycin D | 81.9 ± 10.2 |

*Data were summarized from four sets of experiments.

Treatment of Jurkat cells with the ch-α-GM2 antibody (anti-GM2) or the ch-α-GM2 antibody conjugated with a scrambled, control peptide (anti-GM2-T15scr) did not induce apoptosis significantly over levels induced by treatment with control human IgG, as a modest 2-fold increase was observed. However, Jurkat cells treated with the anti-GM2-T15 conjugated underwent a significant amount of apoptosis, nearly 8-fold over background and more than 4-fold higher than that induced by the non-conjugated antibody or the control-conjugated antibody. These results confirmed the activity and specificity of T15-conjugated antibody.

Example 5

Generation of Autophilic Peptide Sequences T15-scr, T15-scr2, R24 and R24-Charged Peptides were synthesized as in Example 5. The sequences are given in Table II.

TABLE II

Sequences for Autophillic Binding Peptides

| Name | Sequence (NH2 to COOH) |
|---|---|
| T15 | (SEQ ID NO: 1)<br>ASRNKANDYTTDYSASVKGRFIVSR |
| T15scr or T15s | (SEQ ID NO: 3)<br>SYSASRFRKNGSIRAVEATTDVNSAYAK |
| T15scr2 | (SEQ ID NO: 4)<br>SKAVSRFNAKGIRYSETNVDTYAS |
| R24 | (SEQ ID NO: 5)<br>GAAVAYISSGGSSINYA |
| R24-Charged | (SEQ ID NO: 6)<br>GKAVAYISSGGSSINYAE |

The peptide derived from R24 is difficult to solubilize except in DMSO or alcohol. Using such solubilizers can not only denature the antibody but also makes it difficult to conjugate to hydrophilic regions of the antibody. To overcome this solubility problem the addition and changes of sequence to charged amino acids, as shown in Table II were undertaken. The resultant modified peptide (R24-Charged) was soluble in aqueous buffer, was able to be conjugated to the tryptophane or nucleotide binding sites and preserved self-binding as well as induced apoptosis when conjugated to anti-GM2 antibody. The same amino acids present in the T15 sequence were randomly re-arranged and used to construct a further synthetic peptide; this scrambled sequence (T15scr or T15s), had no self-binding and when conjugated to anti-GM2 antibody did not induce apoptosis (see Example 5, Table I). In like manner, a second, randomly selected sequence, derived from the amino acids of the T15 sequence, was used to generate a synthetic peptide (T15scr2). Unlike the first scrambled sequence, this peptide demonstrated self-binding and when conjugated to anti-GM2 antibody, induced apoptosis in levels higher than the original T15 sequence. Thus, self-binding behavior can be generated, using the same amino acids from the original T15 sequence but arranged in a different order from the original T15. A peptide library generated using these same amino acids, combined with a screen for self-binding could be used to identify other self-binding sequences.

Example 6

Method Of Conjugating Autophilic Peptides To Antibodies (Comparison Of Various Immunoglobulin Conjugation Sites)

Figure 6:
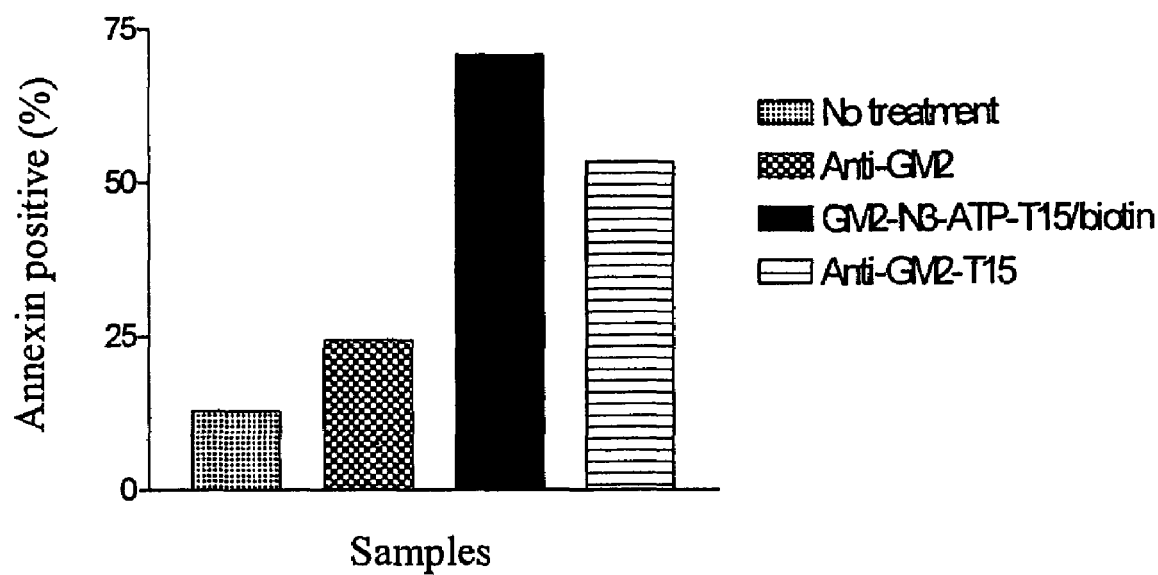
FIG. 6 is a graph comparing the efficacy of autophillic peptide conjugation to an affinity site on an antibody (nucleotide) versus a non-affinity site (CHO-carbohydrate) using anti-GM2.

The T15 peptide sequence was conjugated to anti-GM2 antibody via the nucleotide binding site, tryptophane affinity sites, and through periodate oxidation, the carbohydrate on the Fc region. As shown in FIG. 6, when tested for the ability to trigger apoptosis, the nucleotide site conjugation (GM2-N-3-ATP-T15/biotin) generated a higher level of apoptosis, than the carbohydrate linkage (Anti-GM2-T15). This was in spite of the fact that carbohydrate linkage installed 8-10 peptides per antibody and nucleotide linkage only 2 peptides per antibody. Affinity site conjugation was the best method of conjugation of peptides. Conjugation to epsilon-amino acids of antibody, via hetero-bifunctional cross-linking agents, gave an inactive conjugate (not shown).

Example 7

Restoration of Apototic Activity

Figure 5:
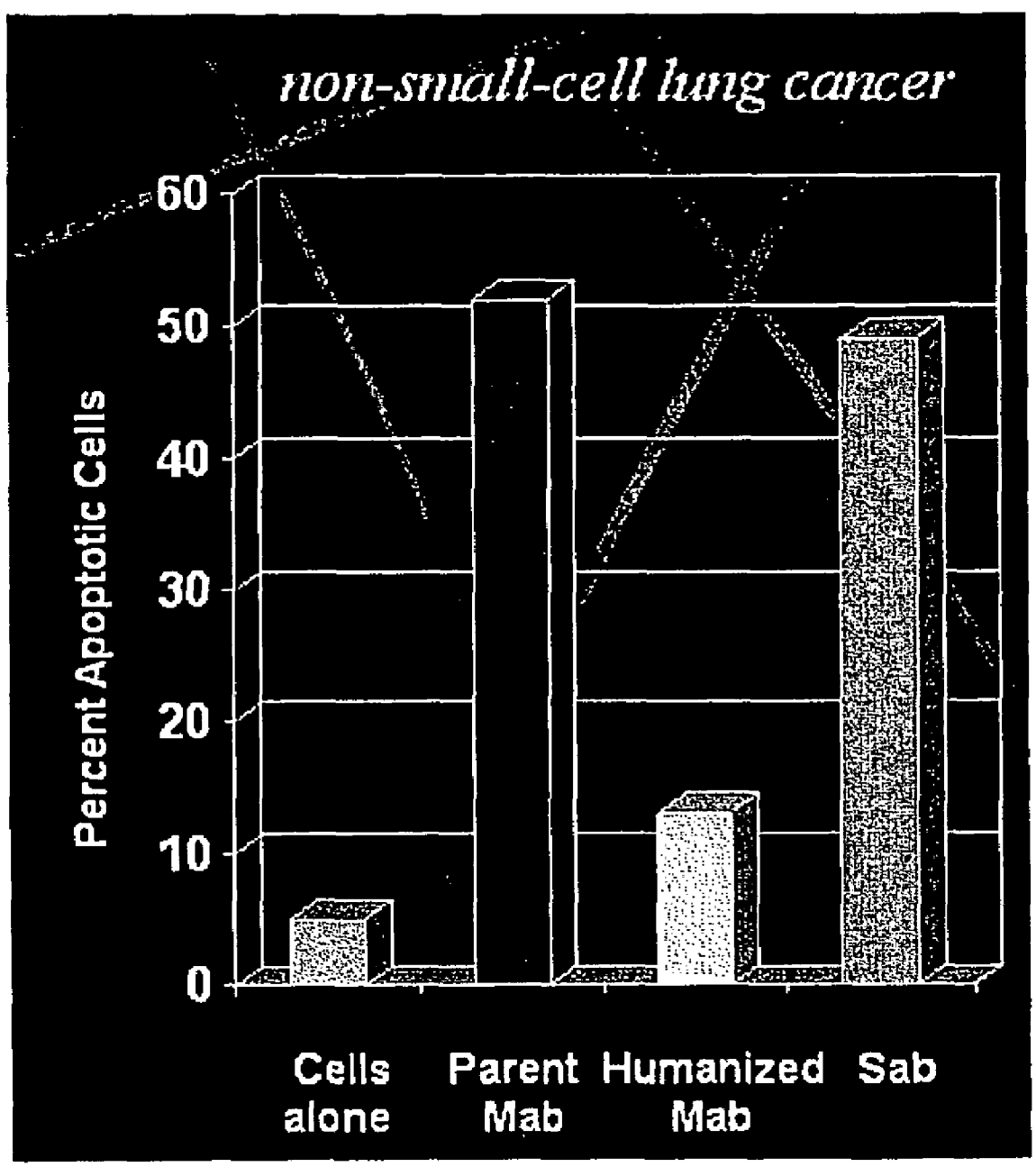
FIG. 5 is a graph depicting enhanced apoptosis of tumor cells using anti-GM2 antibody conjugated with T15 peptide.

A parental antibody to GM2 glycolipid, derived from a non-human hybridoma, was tested for the ability to trigger apoptosis against human cancers including non-small cell lung cancer (FIG. 5). The parental antibody demonstrated a high level of apoptosis and killing of cancer cells. The antibody was also effective in inhibiting growth of cancers in nude mouse models (not shown). To remove the potential for immunogenicity in humans, the antibody was "humanized" via cloning the heavy and light chain CDR's into the context of a human IgG1. Despite retention of affinity and specificity (not shown), the humanized antibody demonstrated much reduced ability to trigger apoptosis. In contrast, the humanized antibody, conjugated to a self-binding peptide (Sab), demonstrated high levels of apoptosis, similar to that of the parental antibody.

A further example is of a murine antibody, R24 which targets the GD3 ganglioside on human melanoma cells. When naturally expressed, this antibody has self-binding and therapeutic activity in patients, but as a humanized antibody it loses avidity, self-binding and therapeutic activity (Chapman et al., 1994). Restoration of therapeutic activity of the humanized R24 antibody can also be achieved by conjugation of a self-binding peptide to the antibody.

The humanized versions of antibody TEPC-15 and T15/S107 will also benefit from conjugation with a self-binding peptide to restore or enhance self-binding and therapeutic activity.

Example 8

Enhanced Binding and Tumor Recognition by Herceptin SuperAntibody

Figure 8:
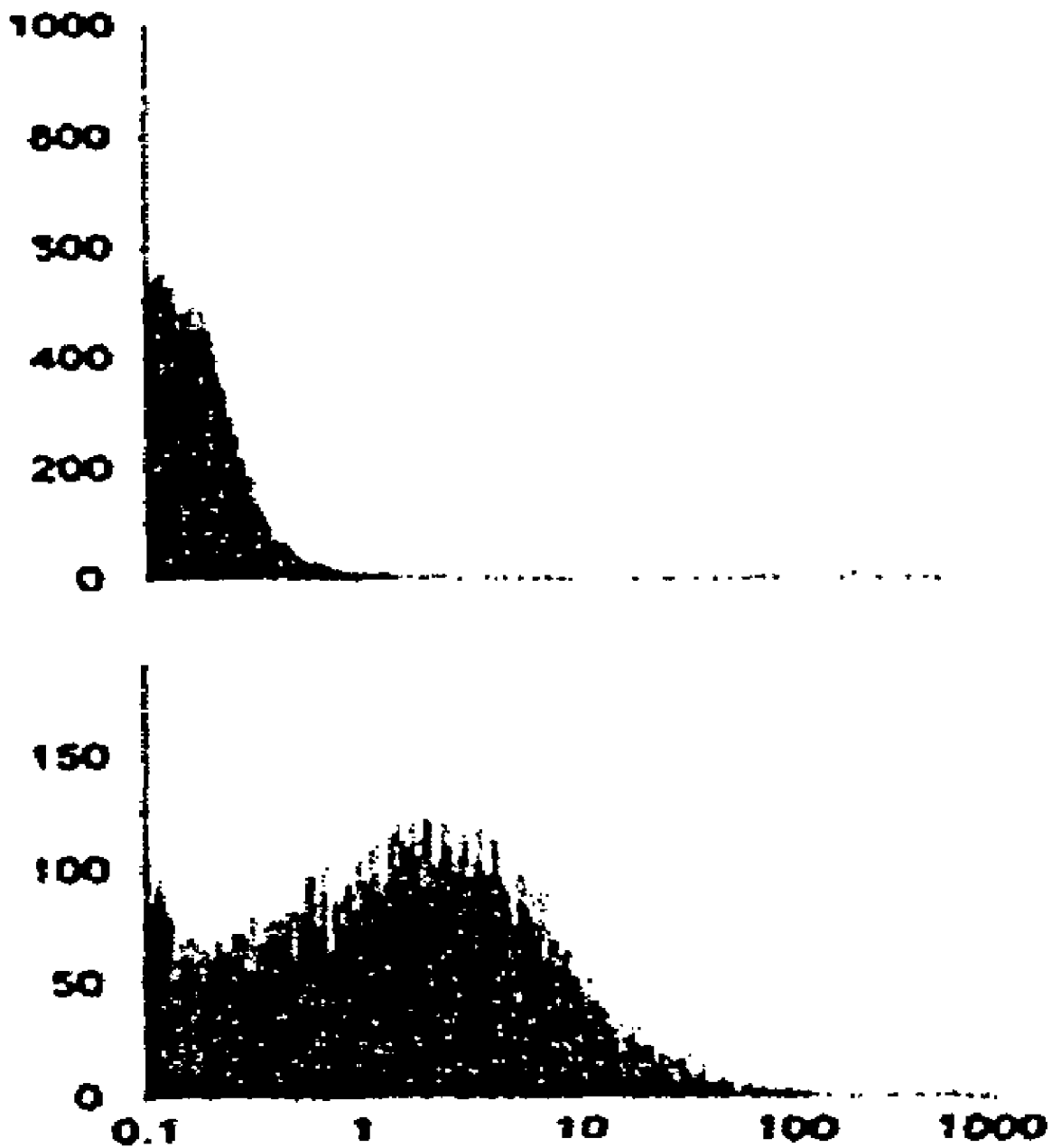
FIG. 8 is a graph comparing the binding of Herceptin (upper panel) and the autophilic peptide conjugated form of Herceptin (lower panel) to small cell lung cancer cells.

Herceptin (monoclonal antibody to HER2/neu), has been approved by the FDA for treatment of breast cancer. The antigen is expressed in approximately 30% of breast cancers but in only about half of those patients is the level of expression sufficient to trigger therapeutic effects. In fact, patients are normally pre-screened in a diagnostic test to determine their suitability for treatment. HER2/neu is also expressed on other cancers, such as non-small cell lung cancer but typically in only low levels, making this type of cancer unsuitable for treatment. We conjugated an autophillic peptide to Herceptin and tested for ability to bind non-small cell lung cancer. As shown in FIG. 8 (top panel), Herceptin reacts very weekly to this cancer; only 0.5% of cells are positive compared to an irrelevant antibody. In contrast, the same cancer can be better detected with the autophilic peptide conjugated form (i.e. SuperAntibody form) of Herceptin; over 57% are positive compared to irrelevant antibody (bottom panel). In separate tests, a SuperAntibody form of Herceptin also inhibited growth better than the parent antibody and could trigger apoptosis unlike the parent.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

The pertinent disclosures of the following references are incorporated herein by reference:

1. Caldas C, Coelho V, Kalil J, Moro A M, Maranhao A Q, Brigido MM, "Humanization of the anti-CD18 antibody 6.7: an unexpected effect of a framework residue in binding to antigen," *Mol. Immunol.* 39(15):941-52, May 2003.
2. Chapman P B, Gillies S D, Houghton A N, Reilly R M, "Mapping effector functions of a monoclonal antibody to GD3 by characterization of a mouse-human chimeric antibody," *Cancer Immunol. Immunother.* 39(3):198-204, September 1994.
3. Dean G A, LaVoy A, Burkhard M J, "Peptide mapping of feline immunodeficiency virus by IFN-gamma ELISPOT," *Vet. Immunol. Immunopathol.* 100(1-2):49-59, July 2004.
4. Ghetie M A, Picker L J, Richardson J A, Tucker K, Uhr J W, and Vitetta E S, "Anti-CD19 inhibits the growth of human B-cell tumor lines in vitro and of Daudi cells in SCID mice by inducing cell cycle arrest," *Blood* 1994;83:1329-1336.
5. Ghetie M A, Podar E M, Ilgen A, Gordon B E, Uhr J W, and Vitetta E S, "Homodimerization of tumor-reactive monoclonal antibodies markedly increases their ability to induce growth arrest or apoptosis of tumor cells," *Proc. Natl. Acad. Sci. USA* 94: 7509-7514, 1997.
6. Gonzales N R et al., "SDR grafting of a murine antibody using multiple human germline templates to minimize its immunogenicity," *Mol. Immunol.* 41(9):863-72, July 2004.
7. Hakenberg J, et al., "MAPPP: MHC class I antigenic peptide processing prediction," *Appl. Bioinformatics*, 2(3):155-8, 2003.
8. Hasbold J, and Klaus G G B, "Anti-immunoglobulin antibodies induce apoptosis in immature B cell lymphomas," *Eur. J. Immunol.* 1990; 20:1685-1690.
9. Isaacs J D and Waldmann H. "Helplessness as a strategy for avoiding antiglobulin responses to therapeutic monoclonal antibodies," *Ther Immunol.* 1(6):303-12, December 1994.
10. Kang, C-Y and Kohler, H., "Immunoglobulin with complementary paratope and idiotype," *J. Exp. Med.* 163: 787, 1986.
11. Kang C Y, Brunck T K, Kieber-Emmons T., et al. "Inhibition of self-binding antibodies (autobodies) by a VH-derived peptide," *Science* 240:1034-6, 1988.
12. Kaveri S V, Halpern R, Kang C Y, and Kohler H., "Self-binding antibodies (autobodies) form specific complexes in solution," *J. Immunol.* 145: 2533-2538, 1990.
13. Kaveri S., Halpern R., Kang C Y., et al., "Antibodies of different specificities are self-binding: implication for antibody diversity," *Mol. Immunol.* 2:733-78, 1991.
14. Kohler H, Paul S., "Superantibody activities: new players in innate and adaptive immune responses," *Immunol. Today* 19: 221-7, 1998.
15. Kohler H., "Superantibodies: synergy of innate and acquired immunity," *Appl. Biochem. Biotechnol.* 83: 1-9, 2000.
16. Leger O J et al., "Humanization of a mouse antibody against human alpha-4 integrin: a potential therapeutic for the treatment of multiple sclerosis," *Mol Immunol.* 39(15): 941-52, May 2003.
17. Lin Y Z, Yao S Y, Veach R A, Torgerson T R, Hawiger J., "Inhibition of nuclear translocation of transcription factor NF-kB by a synthetic peptide containing a cell membrane-permeable motif and nuclear localization sequence," *J Biol. Chem.* 270: 14255-14258, 1995.
18. Miles M A, Wallace G R, Clarke J L, "Multiple peptide synthesis (Pepscan method) for the systematic analysis of B- and T-cell epitopes: Application to parasite proteins," *Parasitol Today* 5(12):397-400, December 1989.
19. Roque-Navarro L. et al., "Humanization of predicted T-cell epitopes reduces the immunogenicity of chimeric antibodies: new evidence supporting a simple method." *Hybrid Hybridomics* 22(4):245-57, August 2003.
20. Schellekens H., "Immunogenicity of therapeutic proteins: clinical implications and future prospects," *Clin Ther.* 24(11):1720-40, November 2002.
21. Suzuki Y., Hirabayashi Y., Matsumoto N., Kato H., Hidari K., Tsuchiya K., Matsumoto M., Hoshino H., Tozawa H., Miwa M. "Aberrant expression of ganglioside and asialoglycosphingolipid antigens in adult T-cell leukemia cells," *Jpn J Cancer Res.* 1987; 78:1112-20.
22. U.S. Pat. No. 5,800,991 for "Nucleotide or nucleoside photoaffinity compound modified antibodies, methods for their manufacture and use thereof as diagnostics and therapeutics," issued to Haley et al., 1998.
23. U.S. Pat. No. 6,238,667 for "Method of affinity cross-linking biologically active immunogenic peptides to antibodies," issued to Kohler, 2001.
24. U.S. Pat. Pub. No. 2003/0103984 of U.S. application Ser. No. 09/865,281, filed May 29, 2001 for "Fusion proteins of biologically active peptides and antibodies."
25. U.S. Pat. No. 6,482,586 for "Hybrid compositions for intracellular targeting," issued to Arab et al., 2002.
26. U.S. Pat. No. 6,406,693 for "Cancer treatment methods using antibodies to aminophospholipids," issued to Thorpe et al., 2002.
27. Veeraraghavan S. et al., "Mapping of the immunodominant T cell epitopes of the protein topoisomerase I," *Ann Rheum Dis.* 63(8):982-7, August 2004.
28. Wallen-Ohman M., Lonnbro P., Schon A., and Borrebaeck C. A. K., "Antibody-induced apoptosis in a human leukemia cell line is energy dependent: thermochemical analysis of cellular metabolism," *Cancer Letters* 1993;75:103-109.
29. Ward R. E., McNamara-Ward M., Webb C. F., Altman D., Lim P. K., Tucker P. W., and Kohler H., "Regulation of an idiotype+B cell lymphoma. Effects of antigen and anti-idiotypic antibodies on proliferation and Ig secretion," *J. Immunol.* 1988; 141:340-345.
30. Zhao Y., D. Lou, J. Burkett and H. Kohler, "Enhanced Anti-B-cell Tumor Effects with Anti-CD20 Superantibody," *J Immunotherapy* 25: 57-62, 2002.

31. Zhao Y., Brown T., Kohler H., and Müller S., "MTS-Conjugated-Antiactive caspase-3 antibodies Inhibit Actinomycin D-induced apoptosis," *Apoptosis* 8(6):631-7, December 2003.

32. Zhao, Y. and H. Kohler, "Enhancing Tumor Targeting and Apoptosis Using Non-Covalent Antibody Homo-dimers", *J Immunotherapy*, 25:396-404, 2002.

What is claimed is:

1. An autophilic antibody comprising an autophilic peptide conjugated to an immunoglobulin component of a non-autophilic antibody, wherein the autophilic peptide is photocrosslinked to a heterocyclic affinity site or a nucleotide affinity site of the immunoglobulin; or crosslinked to a carbohydrate site of the Fc portion; or crosslinked to an amino or sulfhydryl group of the immunoglobulin, the autophilic antibody comprising one or more functional peptides conjugated to the non-autophilic antibody, wherein the one or more functional peptides comprises SEQ ID NO. 7 and wherein the autophilic peptide is selected from the group consisting of SEQ ID NO. 1, SEQ ID NO. 4, SEQ ID NO. 5, and SEQ ID NO. 6.

2. An autophilic antibody according to claim 1, wherein the one or more functional peptides are conjugated to the non-autophilic antibody at a site that is different from a site that the autophilic peptide is conjugated to the non-autophilic antibody.

3. An autophilic antibody according to claim 1, wherein the non-autophilic antibody is selected from the group consisting of anti-GM2 and anti-caspase antibodies.

4. An antibody conjugate according to claim 1, comprising an anti-GM2 antibody conjugated with the autophilic peptide of SEQ ID NO. 1.

5. An antibody conjugate according to claim 1, comprising a non-human antibody to GM2 glycolipid conjugated with the autophilic peptide of SEQ ID NO. 1, SEQ ID NO. 4, SEQ ID NO. 5, or SEQ ID NO. 6.

6. A composition comprising one or more autophilic antibodies according to claim 1, and a pharmaceutically acceptable carrier.

* * * * *